(12) United States Patent
Shah

(10) Patent No.: US 11,026,700 B2
(45) Date of Patent: Jun. 8, 2021

(54) JIG FOR GUIDING PLACEMENT OF FEMORAL COMPONENT OF THE IMPLANT IN KNEE REPLACEMENT SURGERY

(71) Applicant: Manish Shah, Ahmedabad (IN)

(72) Inventor: Manish Shah, Ahmedabad (IN)

( * ) Notice: Subject to any disclaimer, the term of this patent is extended or adjusted under 35 U.S.C. 154(b) by 77 days.

(21) Appl. No.: 16/326,347

(22) PCT Filed: Jul. 19, 2017

(86) PCT No.: PCT/IN2017/050297
§ 371 (c)(1),
(2) Date: Feb. 18, 2019

(87) PCT Pub. No.: WO2018/216026
PCT Pub. Date: Nov. 29, 2018

(65) Prior Publication Data
US 2019/0216472 A1    Jul. 18, 2019

(30) Foreign Application Priority Data
May 23, 2017    (IN) .............................. 201721018055

(51) Int. Cl.
*A61B 17/58*    (2006.01)
*A61B 17/60*    (2006.01)
(Continued)

(52) U.S. Cl.
CPC .......... *A61B 17/155* (2013.01); *A61F 2/3859* (2013.01); *A61F 2/461* (2013.01); *A61F 2002/3055* (2013.01)

(58) Field of Classification Search
CPC combination set(s) only.
See application file for complete search history.

(56) References Cited

U.S. PATENT DOCUMENTS

| 4,474,177 A | 10/1984 | Whiteside |
| 5,423,822 A | 6/1995 | Hershberger et al. |

(Continued)

FOREIGN PATENT DOCUMENTS

| FR | 2752519 | 2/1998 |
| JP | 3896/MUM2015 | 4/2017 |

OTHER PUBLICATIONS

Examination Report received in counterpart India Patent Application No. 201721018055, dated Oct. 28, 2020, 6 pages.
(Continued)

*Primary Examiner* — Sameh R Boles
(74) *Attorney, Agent, or Firm* — Klarquist Sparkman, LLP

(57) ABSTRACT

The present jig for guiding placement of femoral component of the implant in a knee replacement surgery (J) is a pre-assembled Jig (J) that ensures precision fit femoral implant for knee replacement based on difference of cuts in millimeters instead of the usual angle measurement in degrees. It avoids intrusion of the intramedullary canal substantially decreasing the risks of embolism. It enables the surgeon to use precise values of depth of cuts obtained from a system for obtaining optimum fit implant as described in patent application number 3896/MUM2015. This enables the surgeon to control precisely the placement of the implant in terms of flexion or extension, varus or valgus, internal or external rotation. It also enables precise placement of the four-in-one cutting block simultaneously with the distal femur cut; ensuring precise placement of knee femoral component of the knee implant. This reduces efforts and time taken during surgery.

5 Claims, 24 Drawing Sheets

(51) Int. Cl.
    *A61F 2/00*     (2006.01)
    *A61B 17/15*     (2006.01)
    *A61F 2/38*     (2006.01)
    *A61F 2/46*     (2006.01)
    *A61F 2/30*     (2006.01)

(56) References Cited

U.S. PATENT DOCUMENTS

| | | | |
|---|---|---|---|
| 5,624,444 | A | 4/1997 | Wixon et al. |
| 5,662,656 | A | 9/1997 | White |
| 8,221,430 | B2 | 7/2012 | Park et al. |
| 2013/0116698 | A1* | 5/2013 | Wilkinson ........... A61B 17/157 606/88 |
| 2015/0051602 | A1 | 2/2015 | Uthgenannt et al. |

OTHER PUBLICATIONS

Office Action received in counterpart Eurasia Patent Application No. 201992383 (Russian), dated Nov. 11, 2020, 4 pages, with English abstract.

Intention to Grant received in counterpart EPO Patent Application No. 17 801 790.1-1122, dated May 26, 2020, 69 pages.

Nam et al., *Journal of Arthroplasty*, Mar. 2016, pp. 91-96, 6 pages.

Maderbacher et al., "What is the optimal valgus pre-set for the intramedullary femoral alignment rods in total knee arthroplasty?" *Knee Surgery, Sports Traumatology, Arthroscopy*, Nov. 2017 issue, pp. 3480-3487, 3-page summary, online May 2016, 3 pages.

Malhotra et al., *The Journal of Bone and Joint Surgery*, Jun. 2015, pp. 889-894, 1-page summary, 1 page.

Maderbacher et al., "Appropriate sagittal femoral component alignment cannot be ensured by intramedullary alignment rods," *Knee Surgery, Sports Traumatology, Arthroscopy*, Aug. 2016 issue, pp. 2453-2460, 3-page summary, online Feb. 15, 2015, 3 pages.

Kucukdurmaz et al., "Do Standard Surgical Guides Produce Accurate and Precise Femoral Bone Resections During Total Knee Arthroplasty?" *Surgery International*, Nov. 2015 issue, pp. 225-232, 1-page summary.

International Search Report from corresponding PCT/IN2017/050297, dated Feb. 12, 2018, 5 pages.

Written Opinion from corresponding PCT/IN2017/050297, dated Feb. 12, 2018, 7 pages.

* cited by examiner

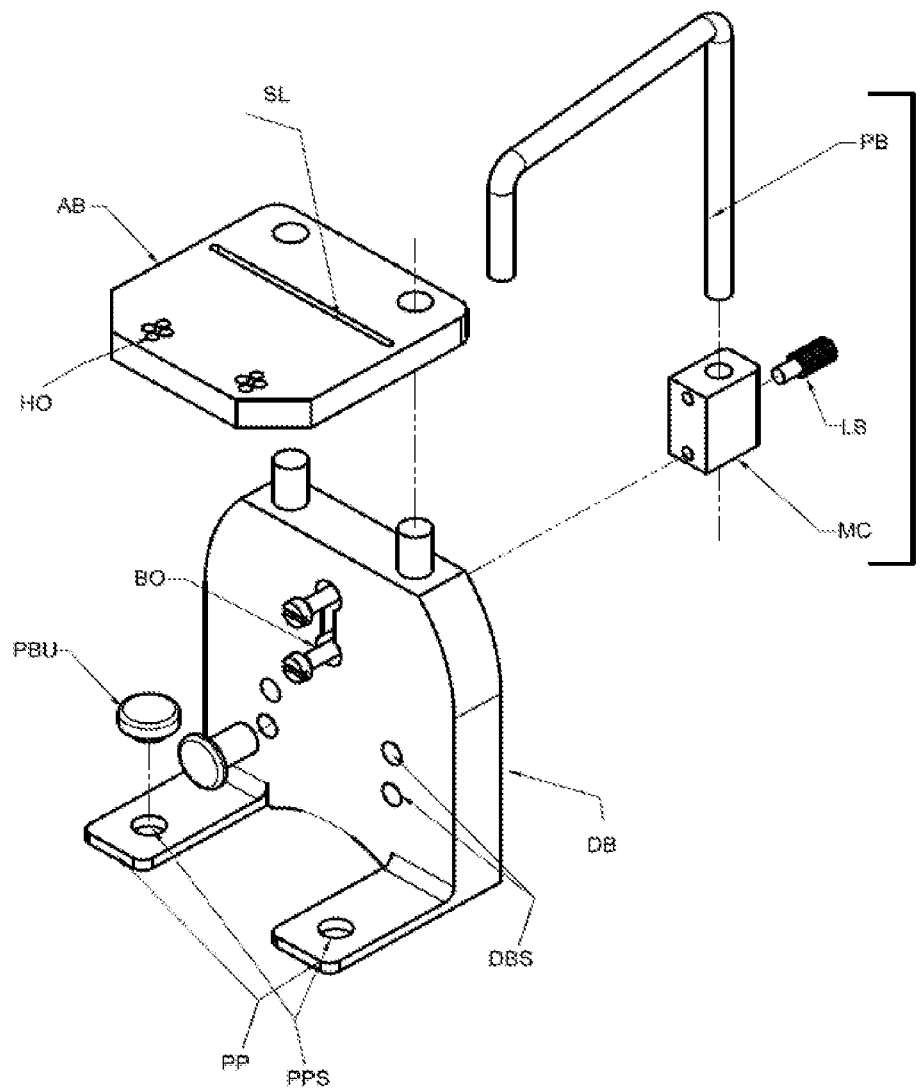
Fig. 1.1

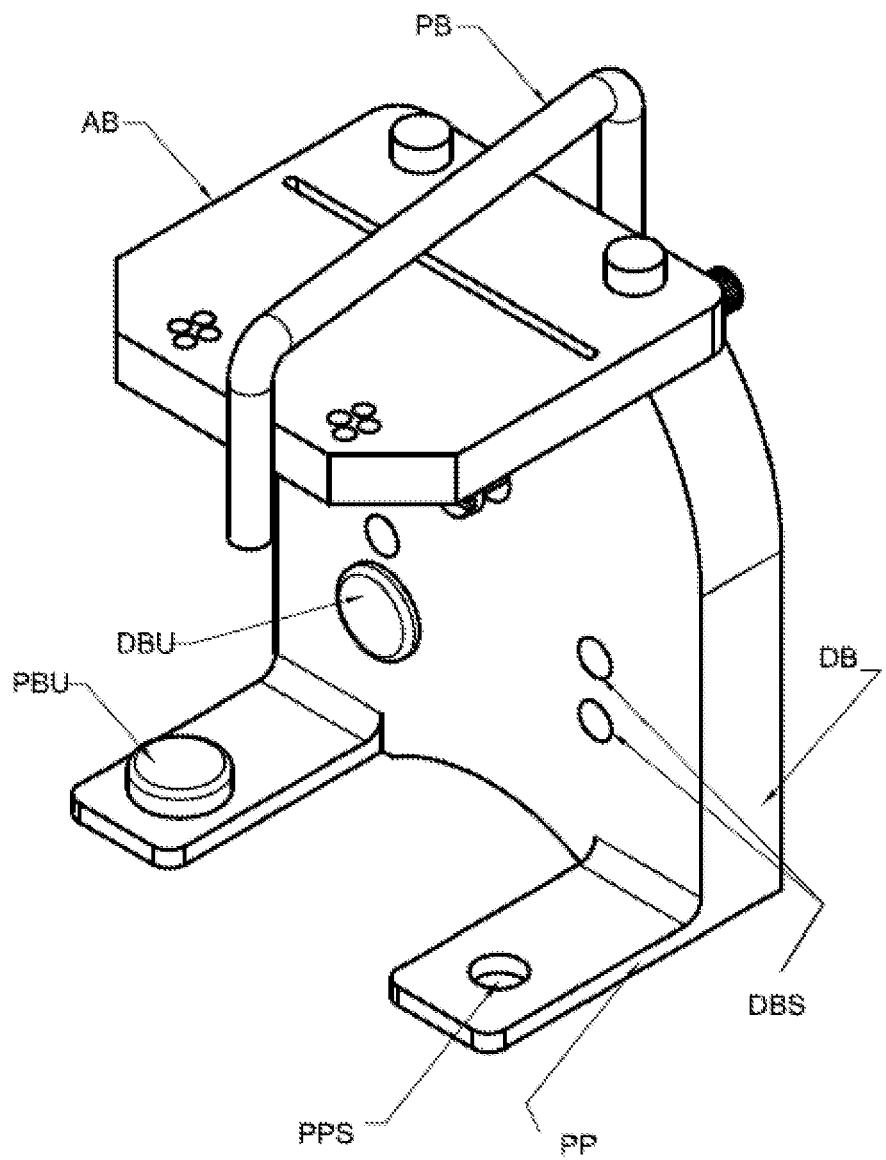
Fig. 1.2

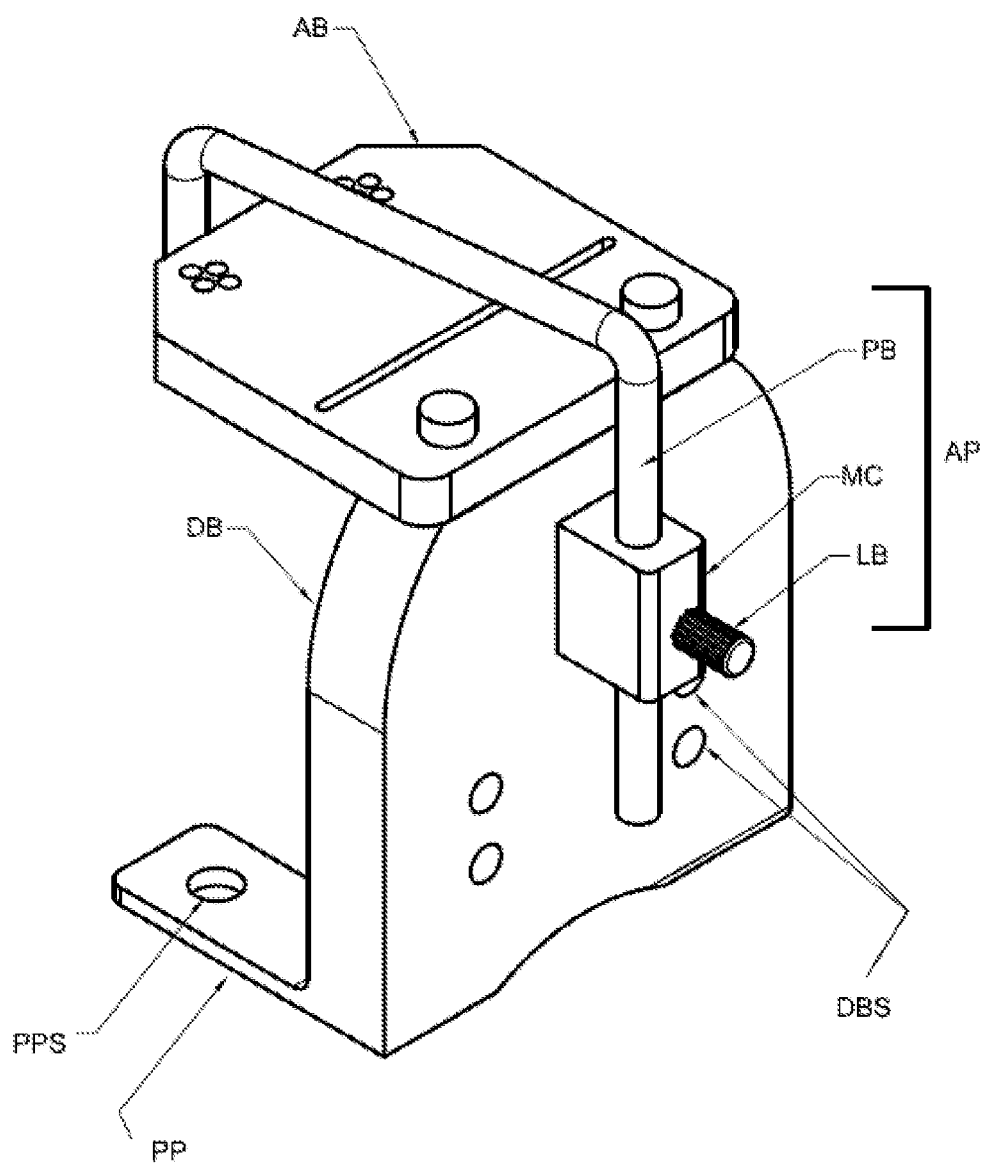
Fig. 1.3

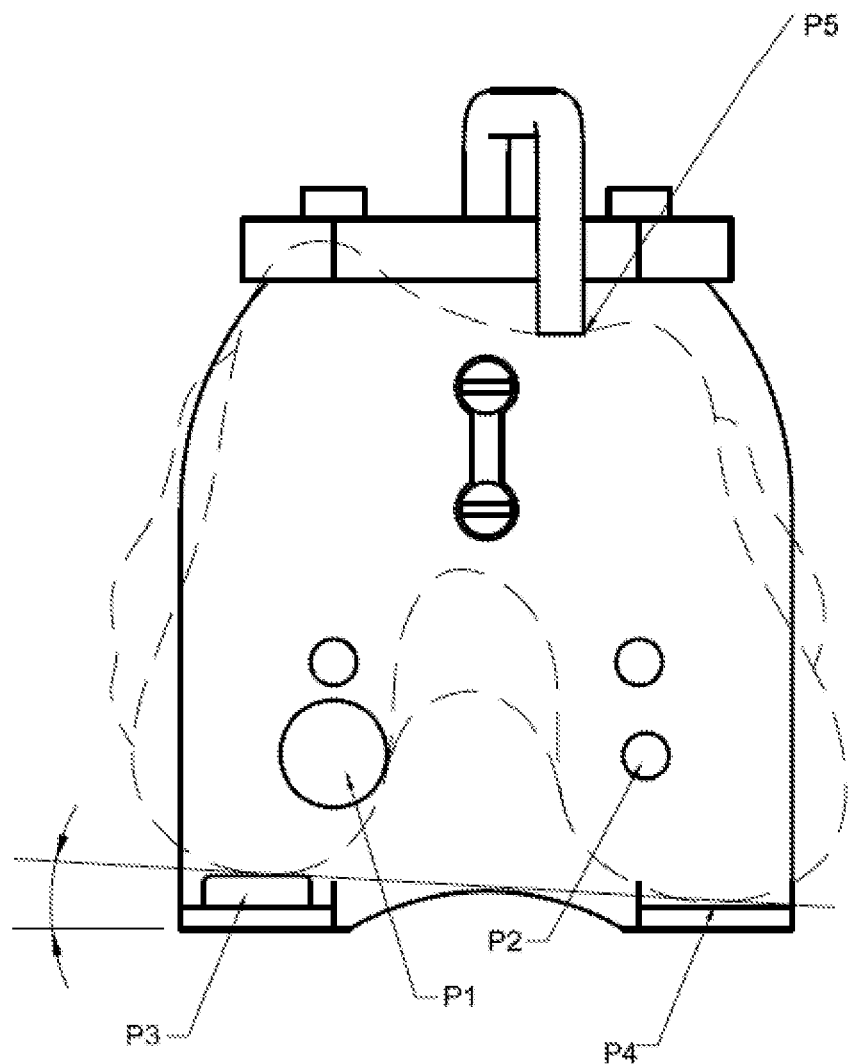
Fig. 1.4

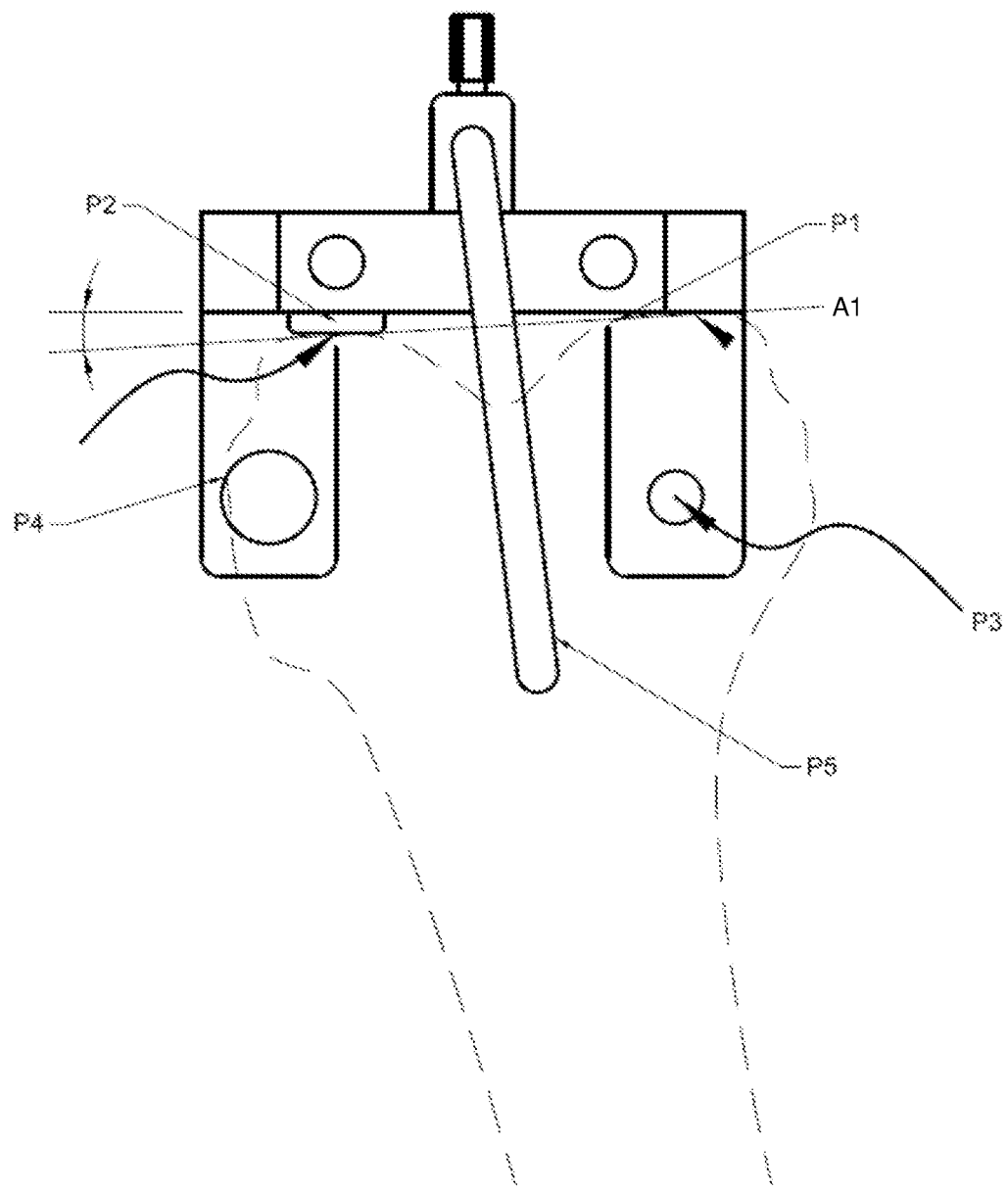
Fig. 1.5

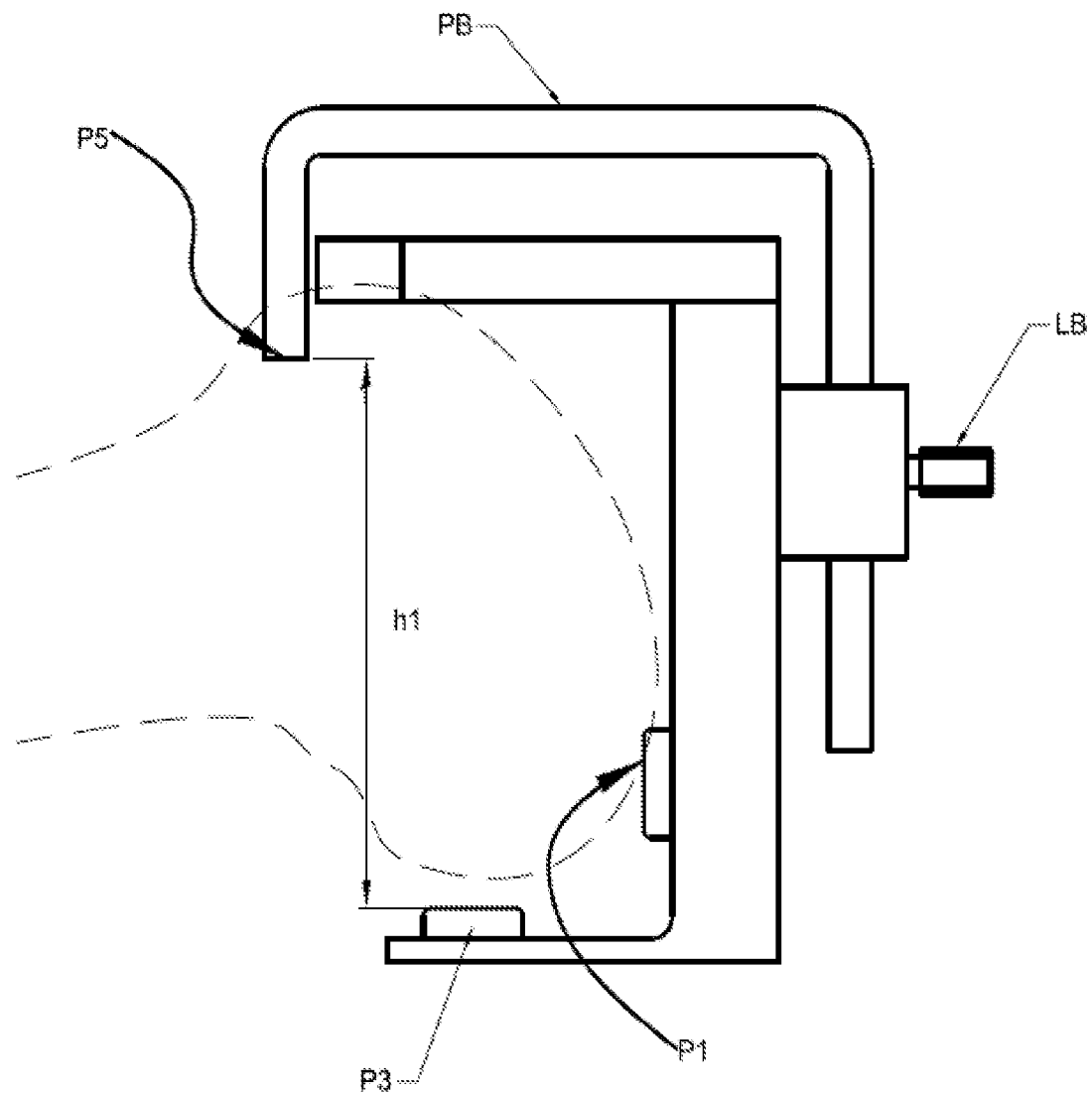
Fig. 1.6

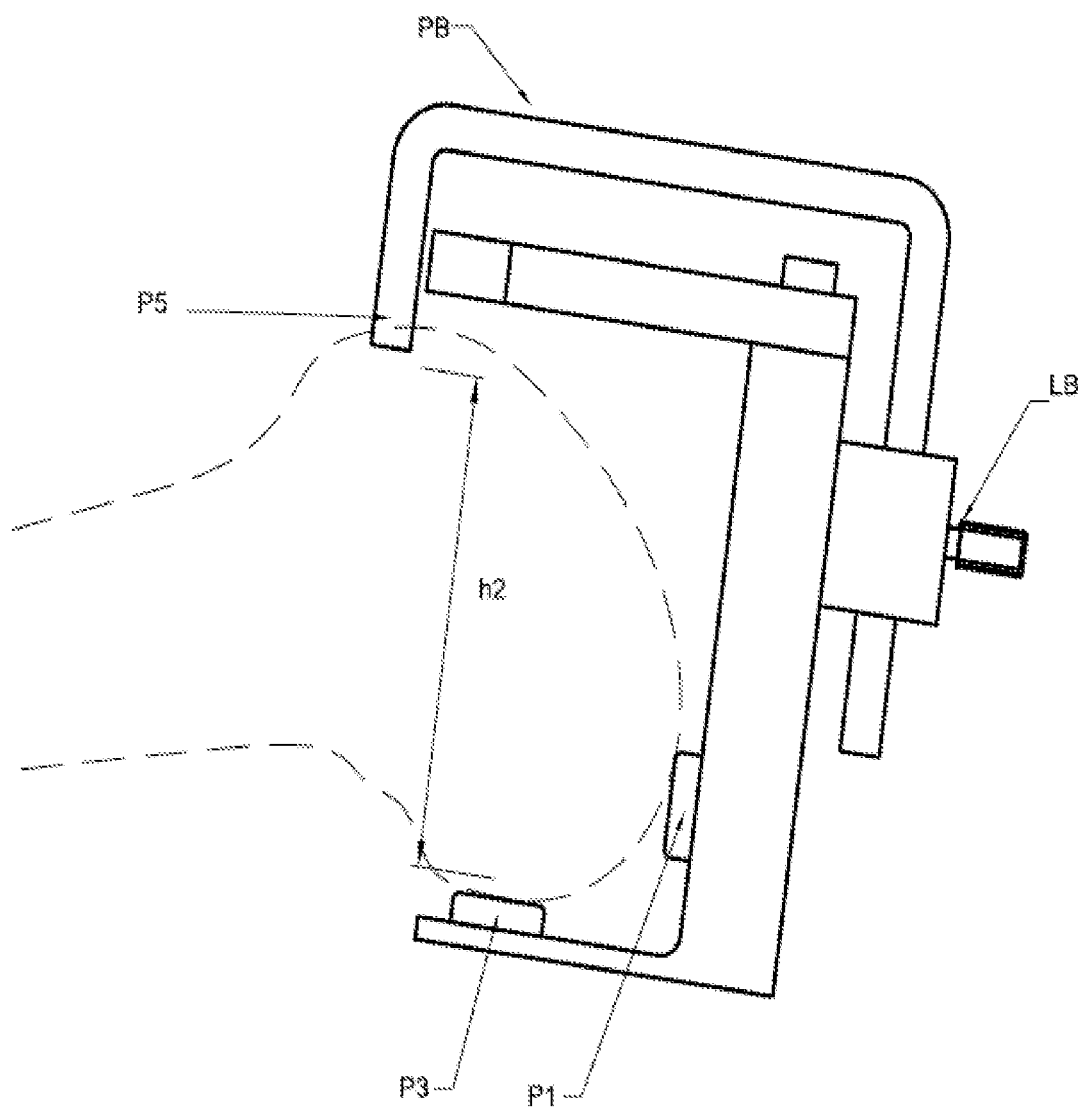
Fig. 1.7

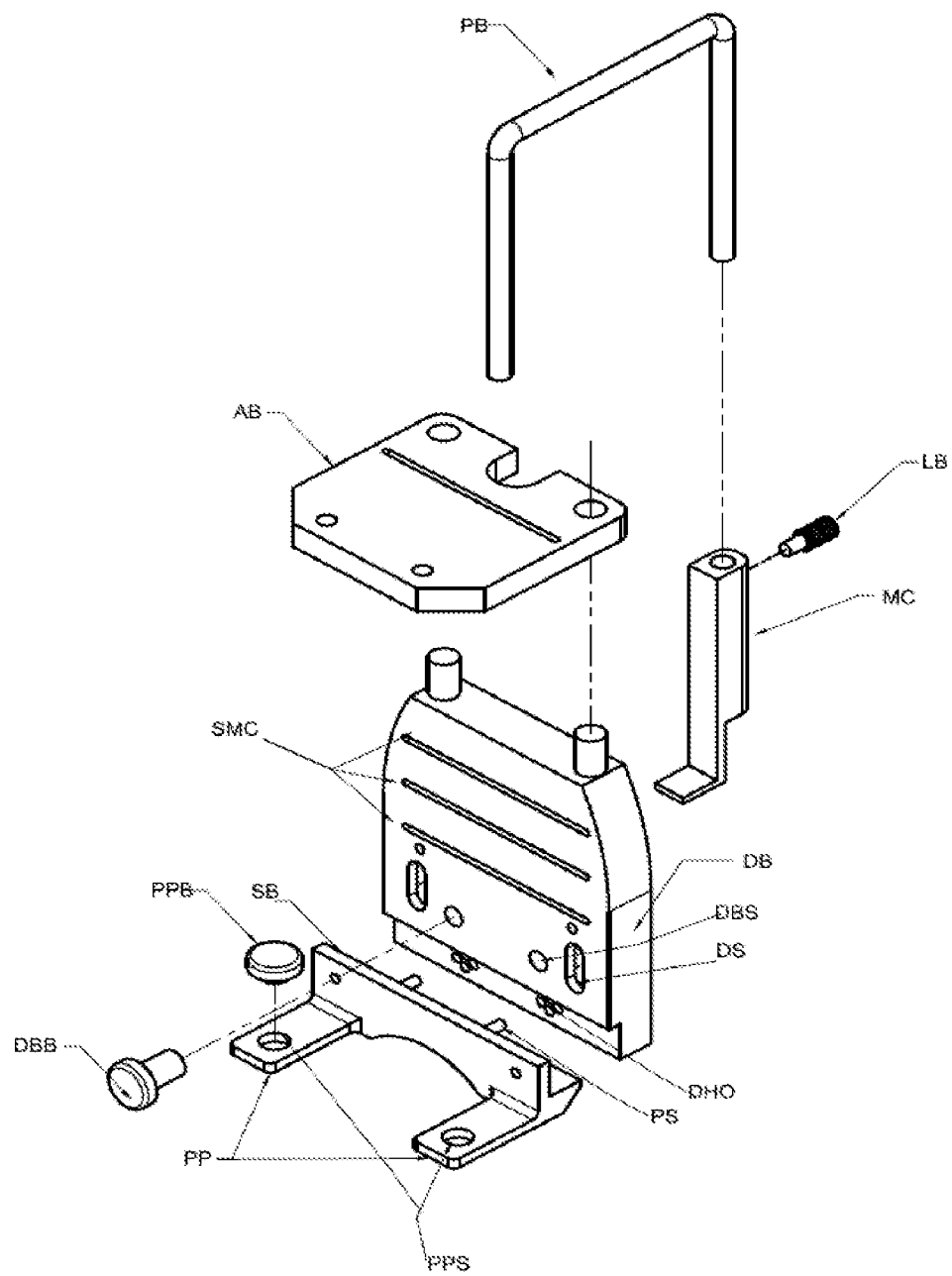
Fig. 2.1

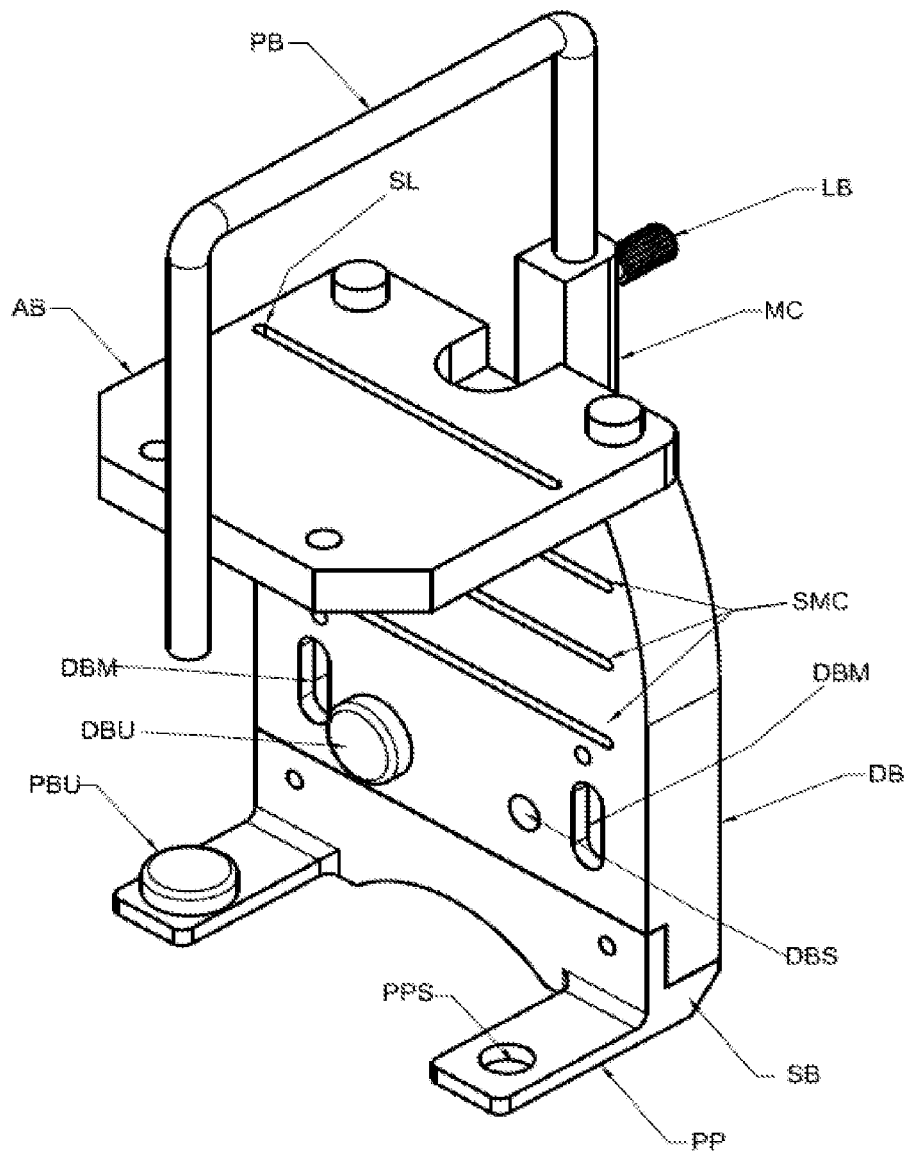
Fig. 2.2

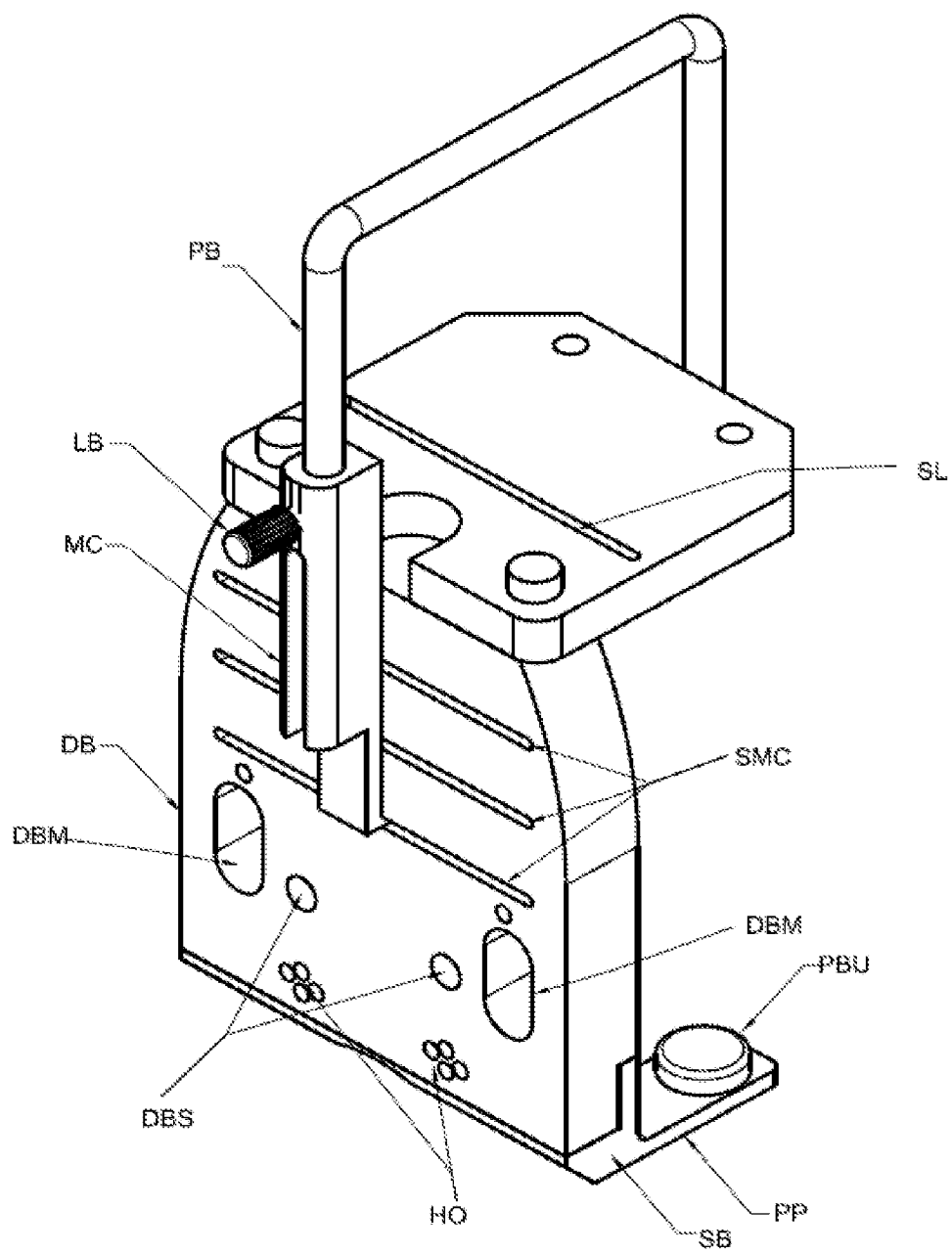
Fig. 2.3

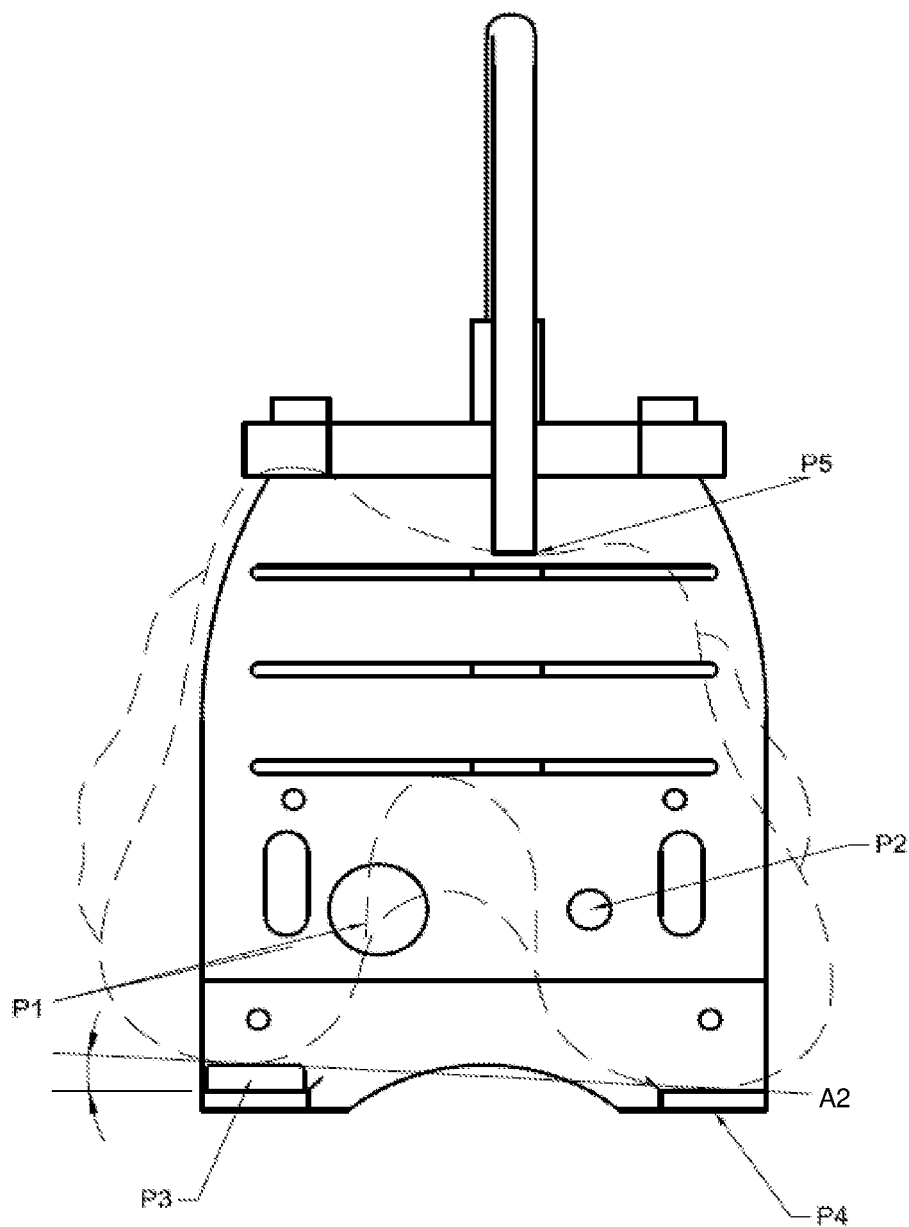
Fig. 2.4

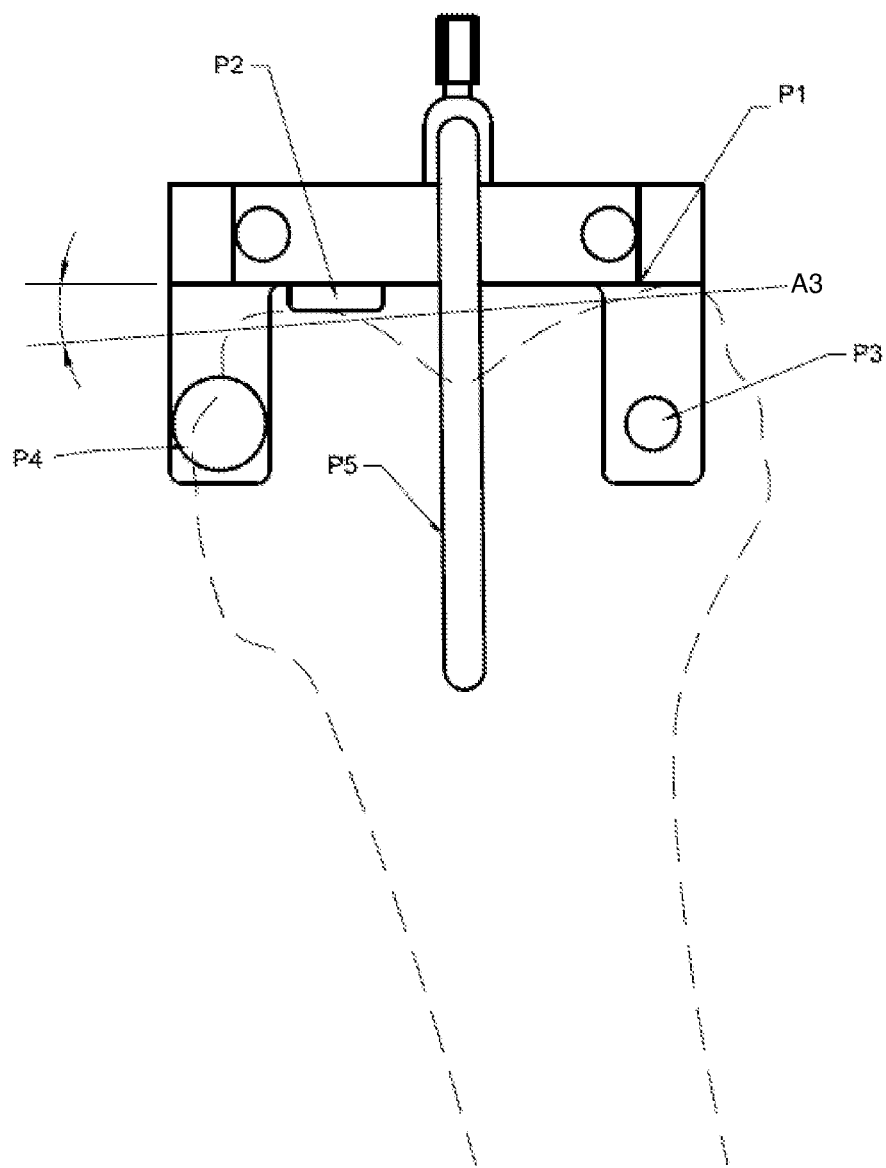
Fig. 2.5

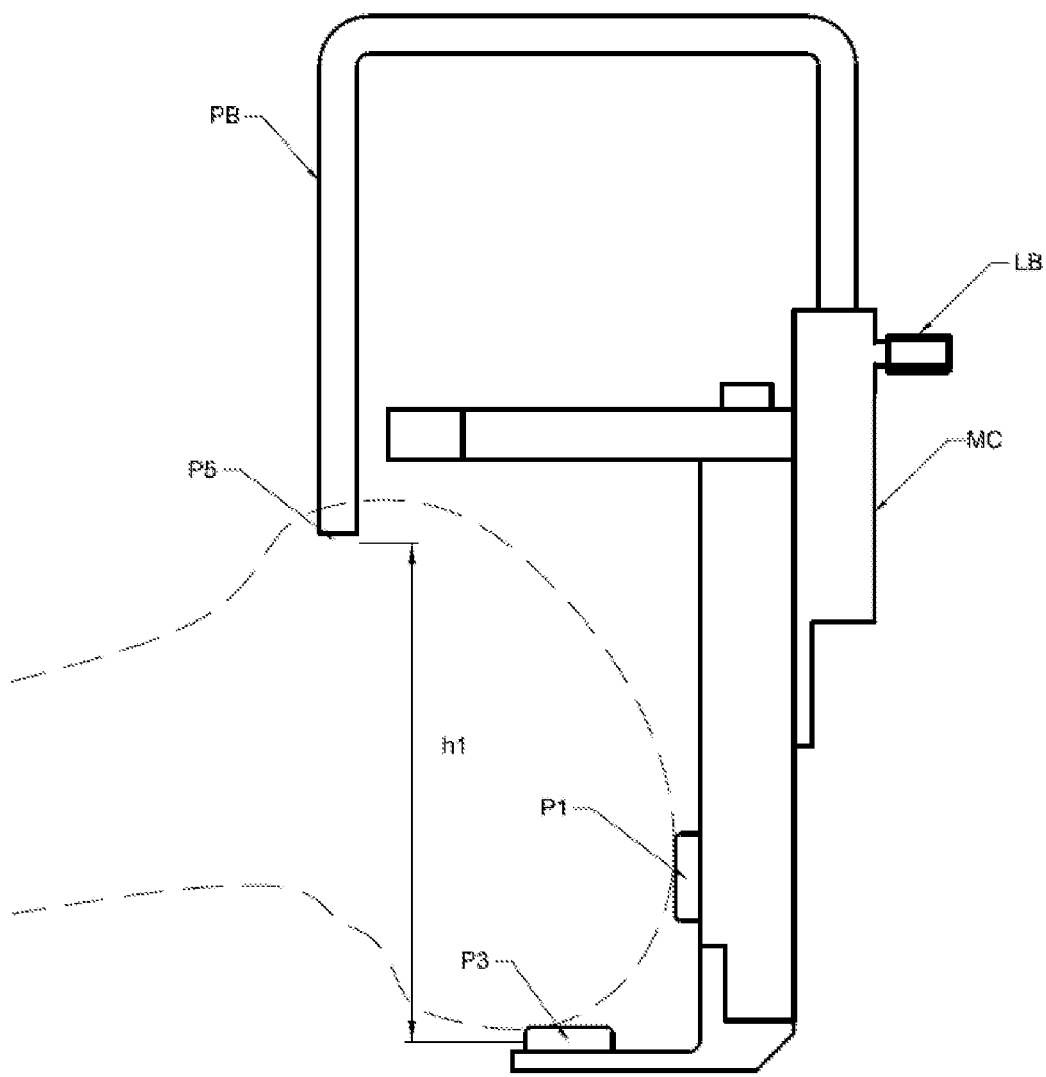
Fig. 2.6

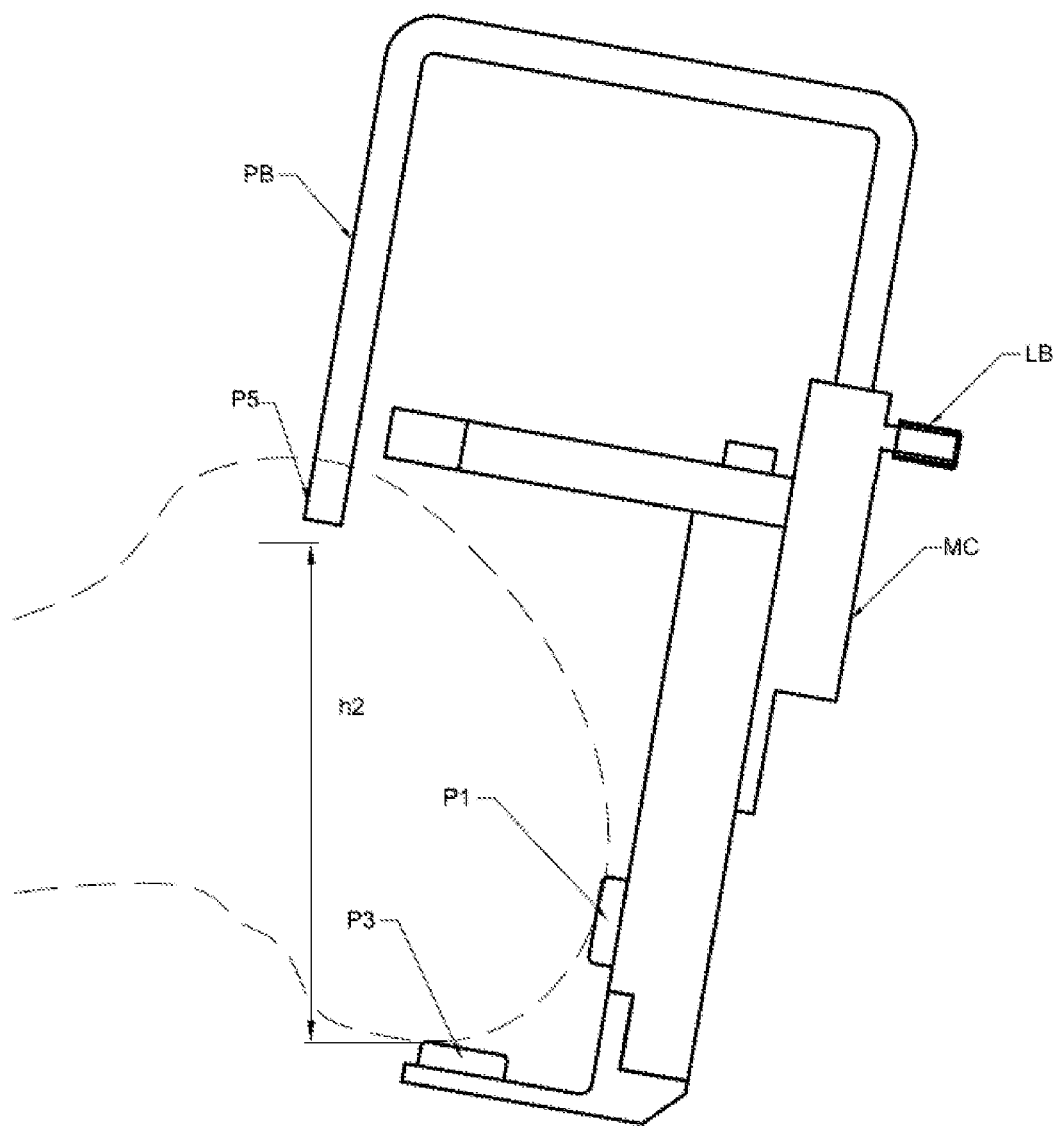
Fig. 2.7

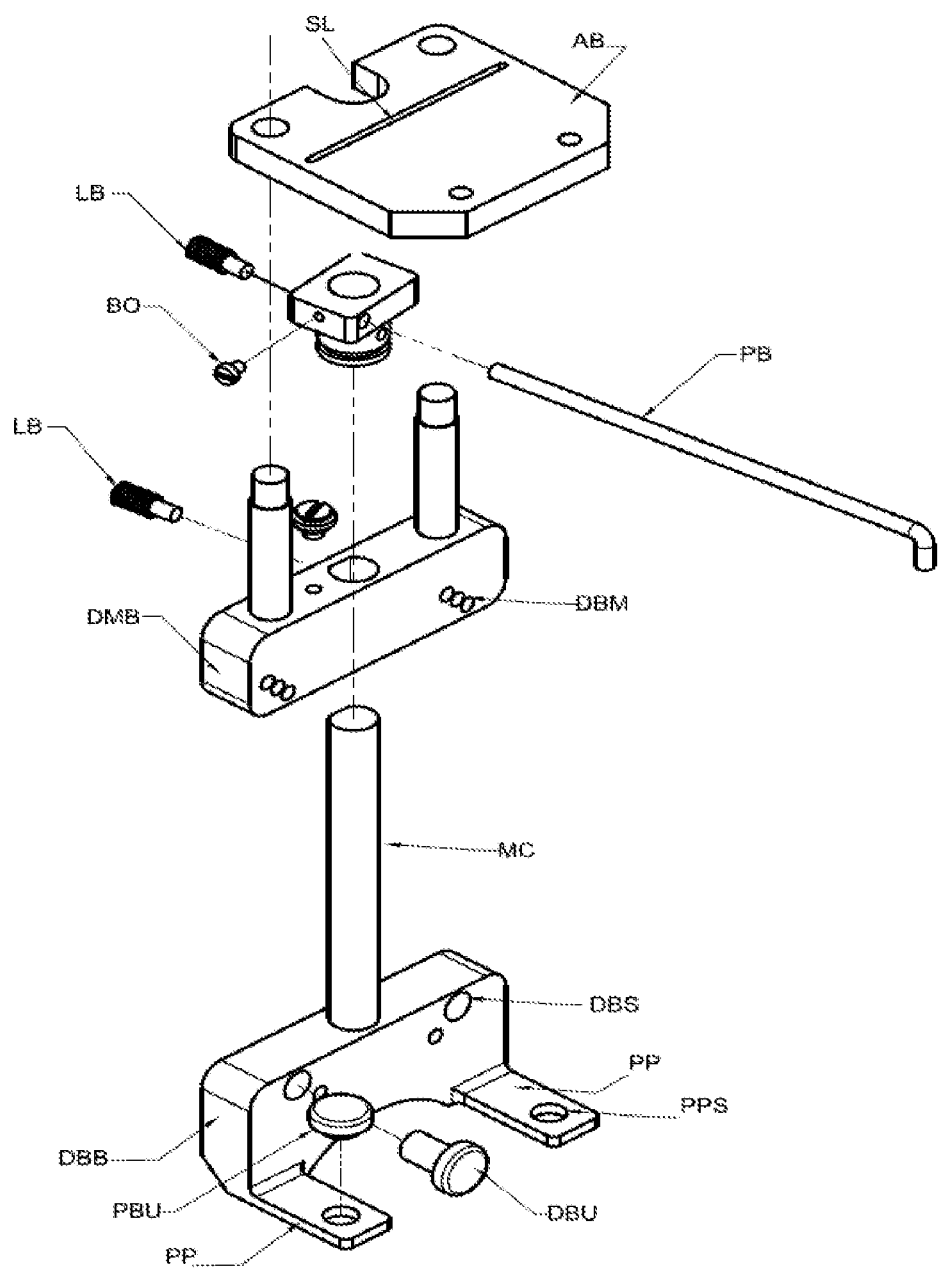
Fig. 3.1

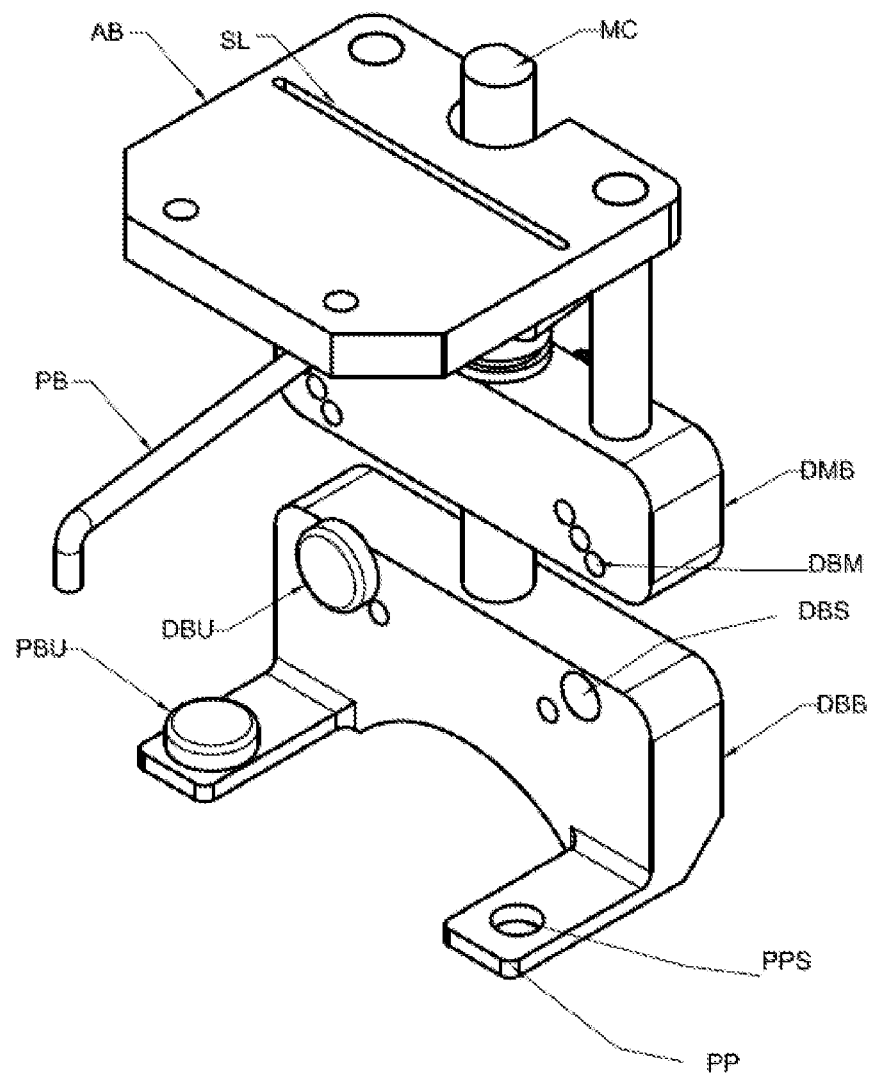
Fig. 3.2

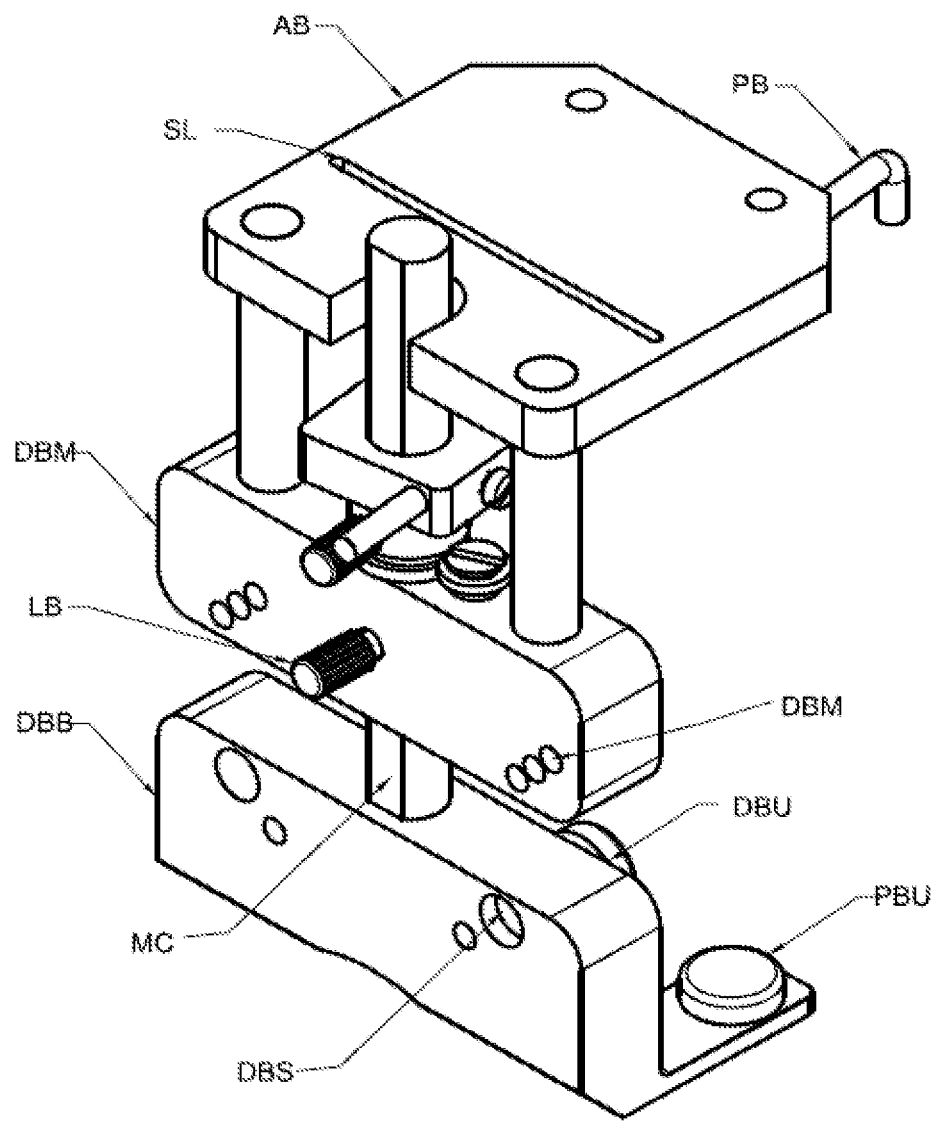
Fig. 3.3

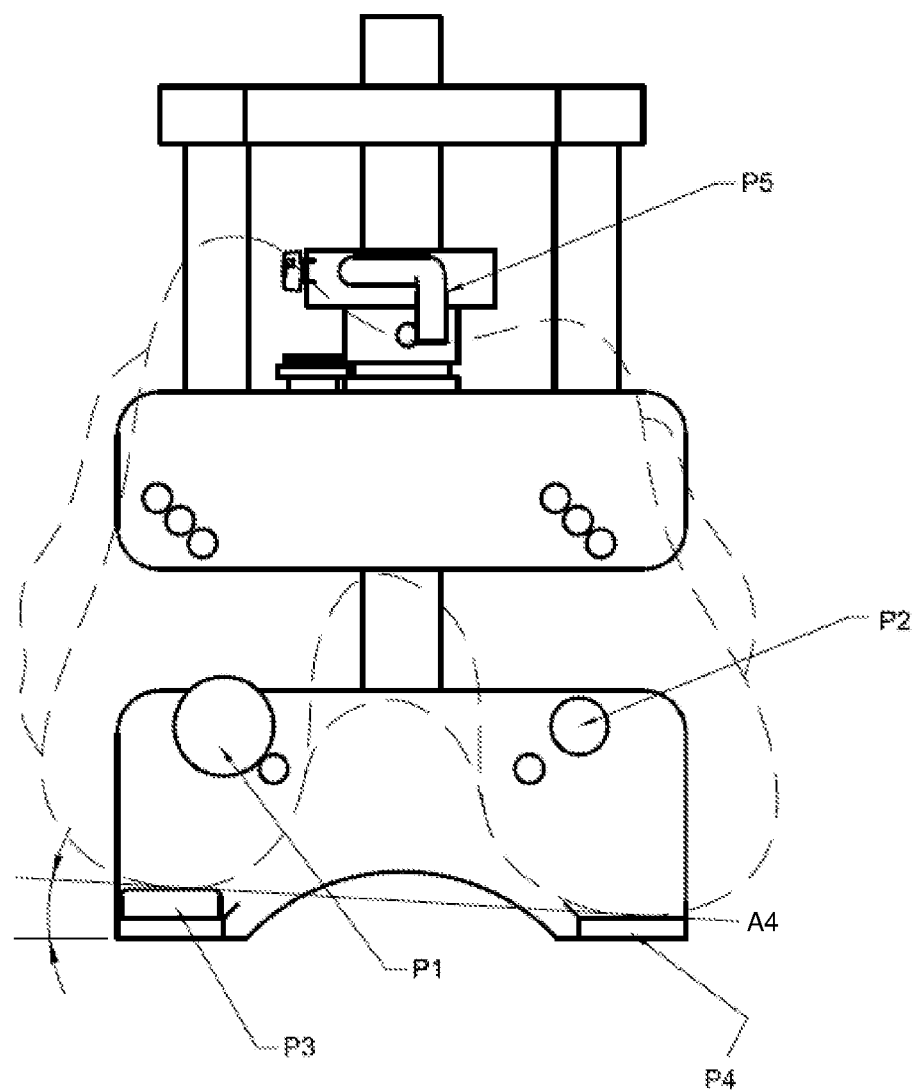
Fig. 3.4

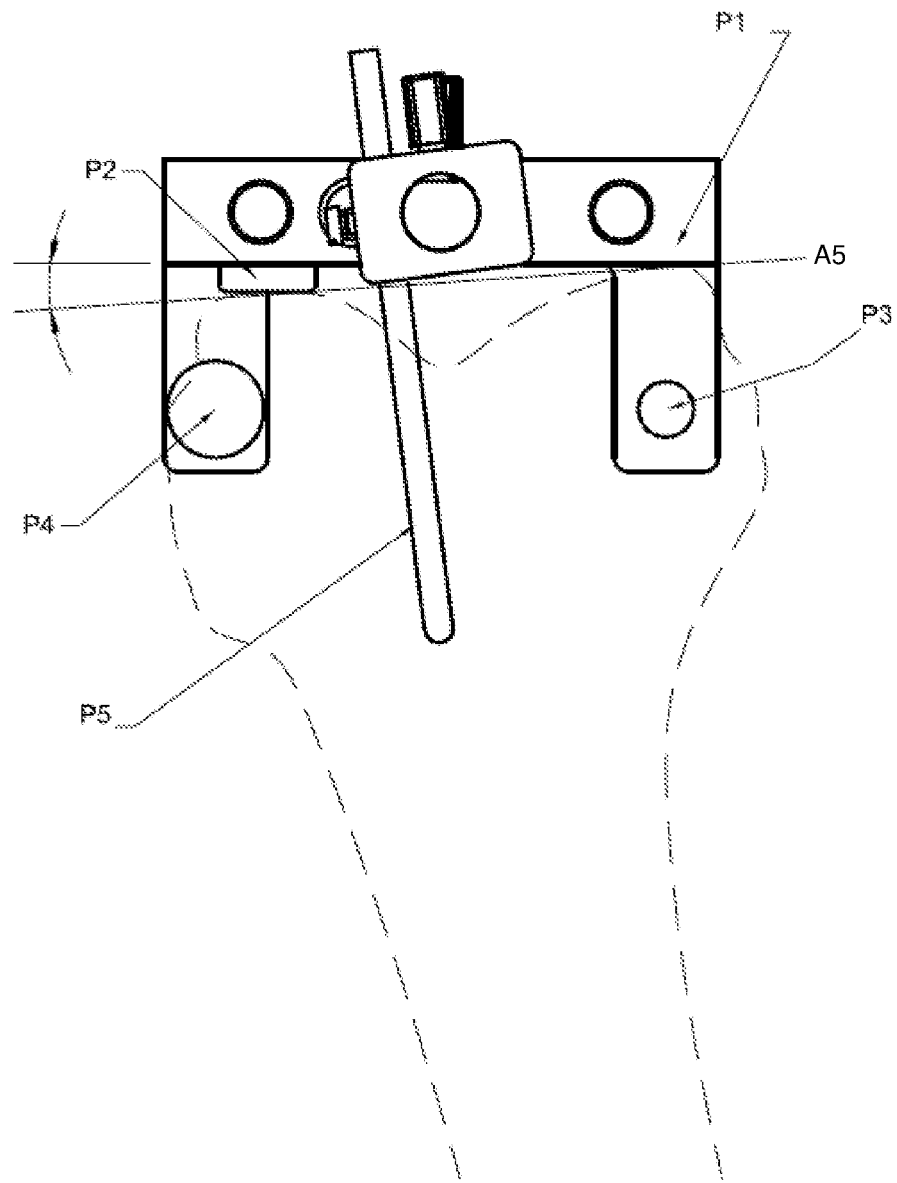
Fig. 3.5

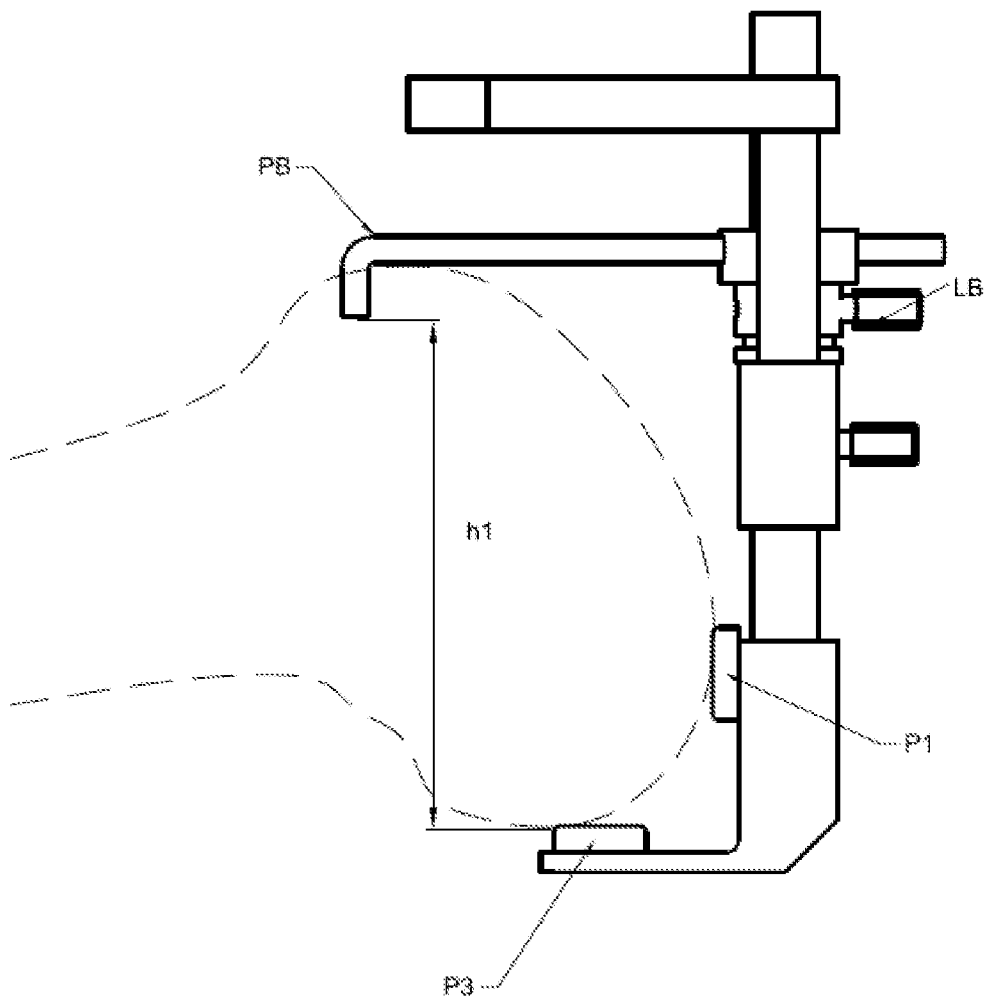
Fig. 3.6

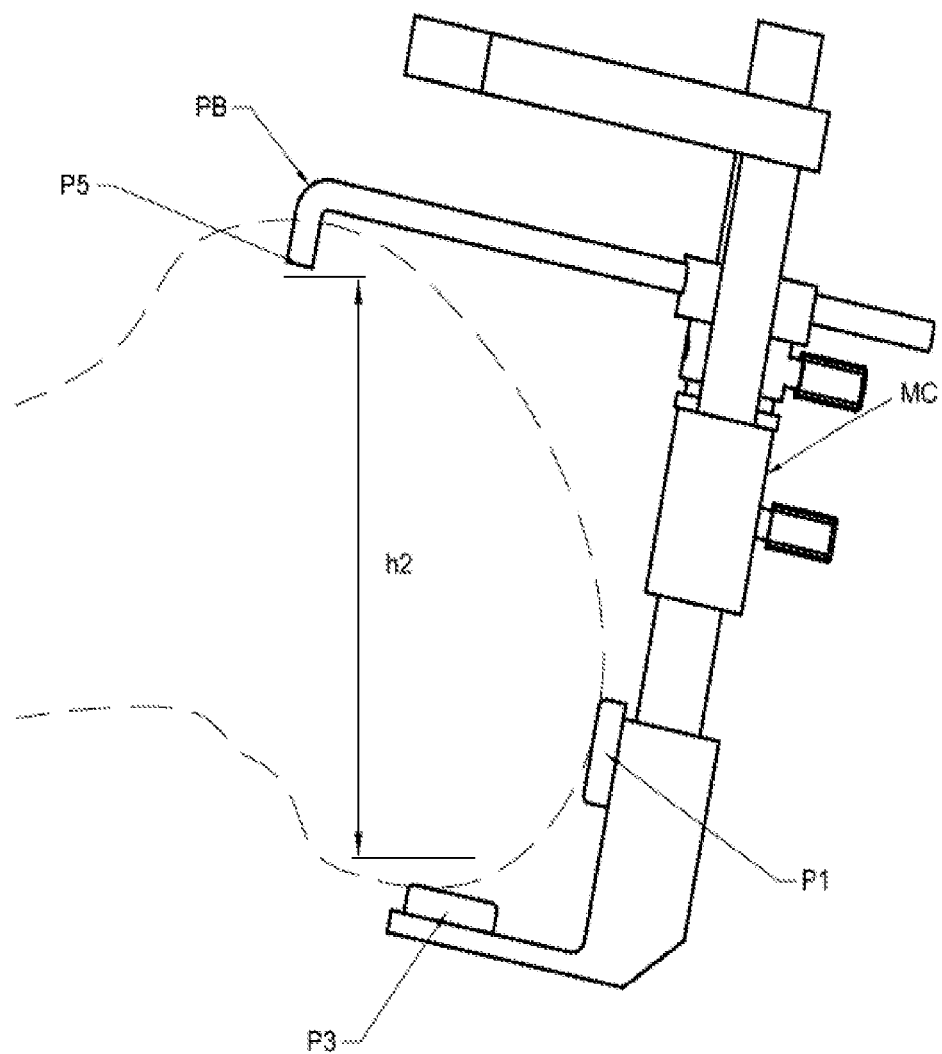
Fig. 3.7

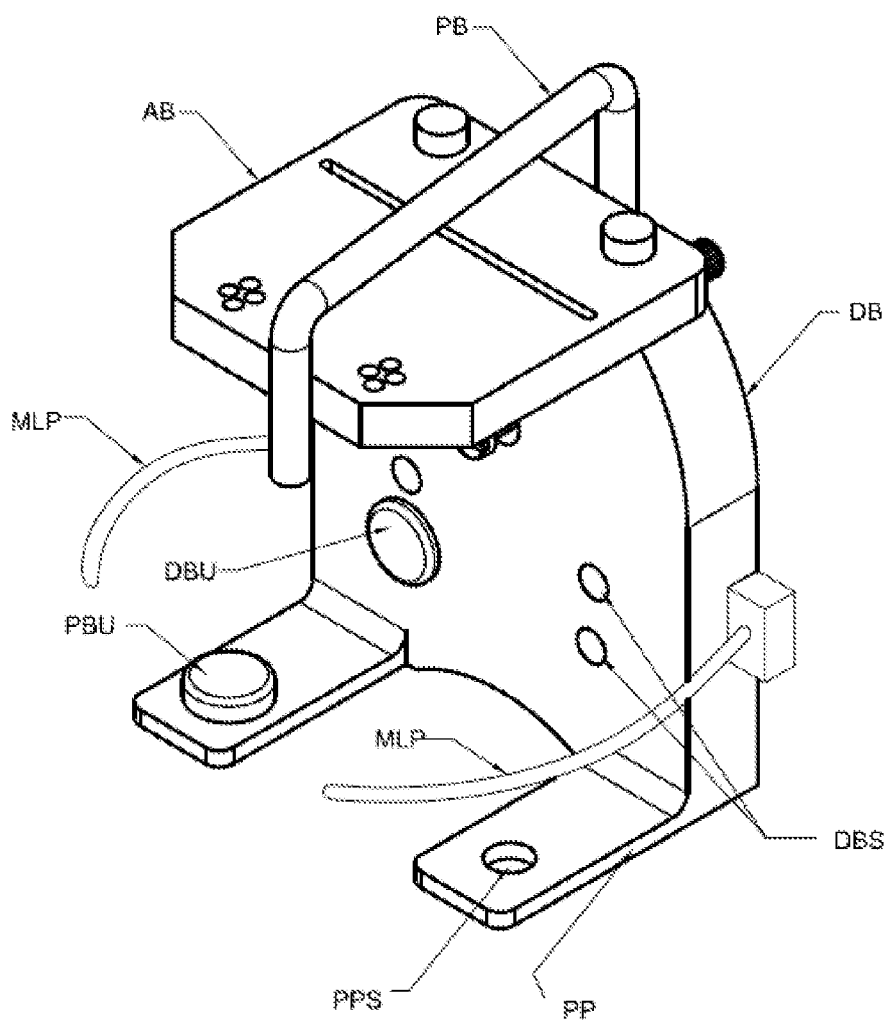
Fig. 4.1

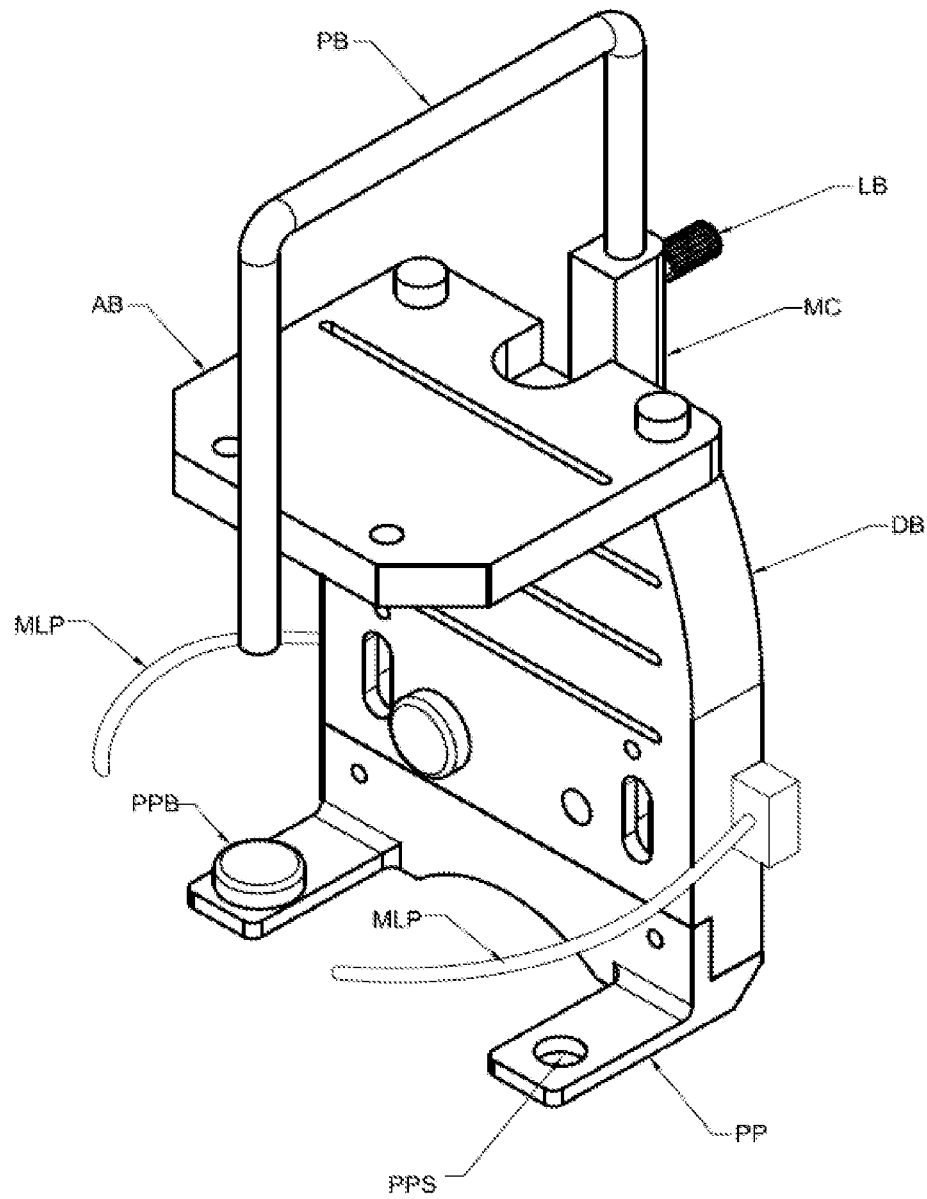
Fig. 4.2

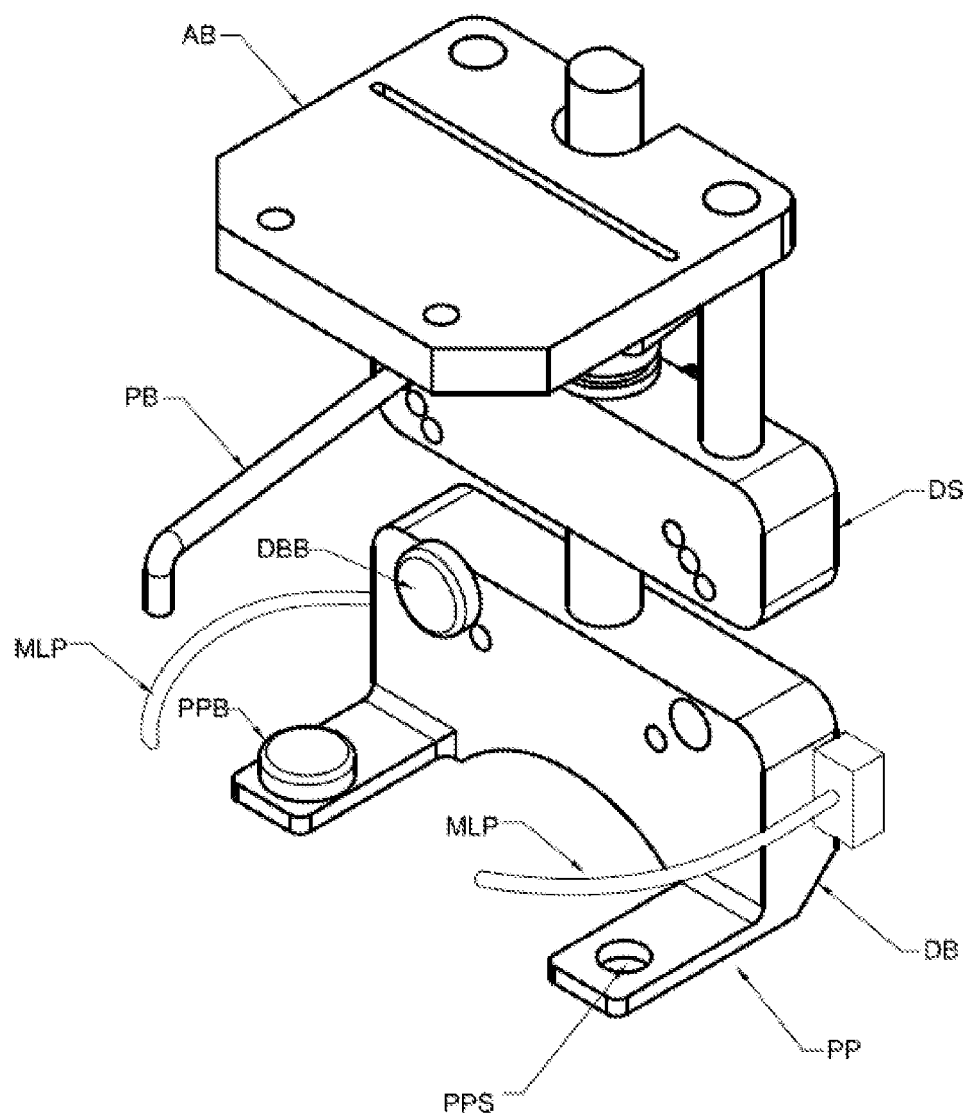
Fig. 4.3

JIG FOR GUIDING PLACEMENT OF FEMORAL COMPONENT OF THE IMPLANT IN KNEE REPLACEMENT SURGERY

CROSS REFERENCE TO RELATED APPLICATIONS

This is the U.S. National Stage of International Application No. PCT/IN2017/050297, filed Jul. 19, 2017, which was published in English under PCT Article 21(2), which in turn claims the benefit of India Application No. 201721018055, filed May 23, 2017, which is incorporated herein by reference in its entirety.

FIELD OF INVENTION

The present invention relates to a jig for guiding a femoral component of knee replacement. In particular, present invention relates to a modular jig which is pre-assembled to ensure precision fit femoral implant for knee replacement based on difference of cuts in millimeters instead of the usual angle measurement in degrees. It avoids intrusion of the intramedullary canal substantially decreasing the risks of embolism. It enables the surgeon to use precise values of depth of cuts obtained from a system for obtaining optimum fit implant as described in patent application number 3896/MUM2015. This enables the surgeon to control precisely the placement of the implant in terms of flexion or extension, varus or valgus, internal or external rotation It also enables precise placement of the four-in-one cutting block simultaneously with the distal femur cut; ensuring precise placement of knee femoral component of the knee implant. This reduces efforts and time taken during the surgery.

BACKGROUND OF THE INVENTION

The knee joint is made up of three bones: femur, tibia and patella. Knee replacement surgery (arthroplasty) is usually necessary when the cartilage covering the three bones of the knee joint (viz., femur, tibia and patella) is worn or damaged to the extent that one's mobility is reduced and one experience pain even while resting. Replacing the damaged knee joint with an optimum fit artificial implant in an optimum position and alignment can help reduce pain and increase mobility.

X-rays are used as standard investigation and planning tools for knee replacement surgeries wherein a single 'snap-shot' of a body part is taken. It provides a two dimensional image of bone for analysis. However, they fail to determine the deformities at certain parts of the bones or between the bones. X-rays also show deformities in varying degrees of magnification. Thus, accurate measurement of the deformities in millimeters cannot be assured using X-rays. The guiding instruments (jigs) used for performing knee replacement were based on observations from X-rays. To overcome the inadequacies of the two dimensional investigation tool like X-ray and magnification errors, the deformities are calculated as angles in degrees. Hence, standard guiding instruments to place the implant in proper position and alignment allowed for changes in degrees.

The X-rays are unable to render a three dimensional surface representation and hence, the standard jigs for the femur bone were referenced of the intramedullary canal in the femur. A hole is made in the end of the femur bone in the knee. A rod is inserted in the femur. And a jig is mounted on the rod at an angle. This angle is either decided arbitrarily by the surgeon or based on the X-ray measurements of angles in degrees between the intramedullary canal axis and the desired mechanical axis of the femur. Besides, the rotation of the jig is uncontrolled and hence the angle is taken in any undefined plane.

Nam D et al published in Journal of Arthroplasty, 2016 September issue, pages 91-6 on comparison of use of a fixed arbitrary angle versus variable distal femur resection angle based on X-rays. They concluded that the use of a variable distal femur resection angle improves femoral component alignment after total knee arthroplasty. Maderbacher G et al published in the journal of Knee Surgery Sports Traumatology Arthroscopy in May 2016 issue on "What is the optimal valgus pre-set for intramedullary femoral alignment rods in total knee arthroplasty?" They concluded that exact component alignment could not be achieved and the X-ray measurements were inadequate.

Insertion of rods in the intramedullary canal of the femur during total knee replacement is also associated with higher risk of embolism (pushing fat and blood globules from the canal into the blood stream which can damage the lungs and heart). Malhotra R et al published in the American issue of Journal of Bone and Joint Surgery, June 2015, pages 889-94 regarding the embolic load during total knee replacement surgery with intramedullary rod. It was found to be higher.

Maderbacher G et al published in journal of Knee Surgery Sports Traumatolgy Arthroscopy in the August 2016 issue, pages 2453-60, on "Appropriate sagittal femoral component alignment cannot be ensured by intramedullary alignment rods." They concluded that intramedullary alignment rods do not ensure a distal cutting block alignment between 0 to 3 degrees of flexion in relation to femoral mechanical axis. The extent of flexion or extension could not be foreseen by the surgeon.

Kucukdurmaz F et published in the Journal of Surgery Technology International, November 2015 issue, pages 225-32 on "Do Standard Surgical Guides Produce Accurate and Precise Femoral Bone Resections during Total Knee Arthroplasty?" They found that none of the three existing instrumentation systems that they tested were within 1 mm of the desired cut resection. Only 30-40% cases were within 2 mm of the desired cut resection with these systems. They concluded that improvements in instrumentation are warranted to increase accuracy and precision.

With the development of technology, Computerized Tomography (CT) scan and Magnetic Resonance Imaging (MRI) scan which are being increasingly used as tools to better understand the diseases/deformities related to knee. CT Scans can reproduce accurate three-dimensional models of the bones with precise surface rendering.

Patient specific jigs uses either pre-operative CT or MRI scans. But, in absence of a tool directly in the hands of a surgeon to plan surgery, the actual surgery is planned by a biomedical engineer sitting in a faraway country. The entire process is controlled by the implant manufacturer through the biomedical engineer, and hence a single design knee is only considered while planning. The biomedical engineer picks landmark positioning based on his skills and local biases. Thus, for the patient, his surgery is planned by a biomedical engineer who would have his limitations and would not be performing the surgery. The operating surgeon is only given the final plan for approval. A patient specific Jig is then 3D printed, sterilized and dispatched to the operating surgeon. After the surgery, this jig has to be discarded as it was specific only for this patient. Thus, there are huge time delays and incremental costs, leading the method into disrepute and lack of widespread use. Hence, reusable, modular, universal instrumentation based on these investigations is needed.

Majority of the surgeons have popularly started using CT Scans and MRIs for diagnosis of deformities. There were no means to analyze and find an optimum fit implant and its optimum position and alignment. The present inventor has developed a system for analyzing and guiding to find an optimum fit implant and its optimum position and alignment for a knee replacement surgery as described in patent application number 3896/MUM2015. However, instrumentation based on these investigations is needed to guide precise placement of femoral component of the knee implant while doing a knee replacement surgery.

PRIOR ART

Various jig based systems for assisting knee replacement surgeries have been applied for patents are disclosed in different patent documents:

U.S. Pat. No. 5,624,444 discloses a set of instruments and method for use in knee replacement surgery, specifically to make the necessary femoral resections is described. The simplified set of instruments allows the necessary femoral resections to be performed with fewer instruments, and with fewer necessary steps for the surge onto take. The set of instruments includes a three-dimensional jig which references the anterior and posterior femoral condyles to allow determinations as to alignment, placement, and prosthesis size before any bone cuts are made. However, it depends on angles in degrees based on X-ray measurements. It compels the surgeon to place the implant in the axis of the intramedullary rod in the lateral view and the surgeon cannot flex or extend the implant.

U.S. Pat. No. 4,474,177 discloses a method and apparatus for preparing the distal surface of a femur to receive a distal femoral prosthesis employing an intramedullary reamer which is used to internally locate the central long axis of the femur, an intramedullary alignment guide which is inserted into the space left in the intramedullary canal upon removal of the reamer and at least one femoral surface modifying instrument which cooperatively engages with a guide handle attached to the intramedullary alignment guide to accomplish the shaping of the distal femoral surface. However, it depends on angles in degrees based on X-ray measurements. It compels the surgeon to place the implant in the axis of the intramedullary rod in the lateral view and the surgeon cannot flex or extend the implant.

U.S. Pat. No. 8,221,430 discloses a method a method of manufacturing an arthroplasty jig from CT scans or MRI scans. A 3D model is generated from the CT scan or MRI scan. The surface model is generated and patient specific jig is contoured on the bone surface. These jigs can then be manufactured. However, these jigs can be used for that specific patient only and have to be discarded. There would be time delays between CT scan and manufacturing of the jig and there would be incremental costs.

DISADVANTAGES OF THE PRIOR ART

Various jig based systems available for assisting the knee replacement are available. However, they suffer from at least one of the following disadvantages:

They fail to provide precision in placement of femoral component of the implant on the femur in terms of position and alignment; in a knee replacement surgery.

Generally followed protocols of knee replacement surgeries that work on two dimensions; wherein the rotation of the jig is uncontrolled and hence the angle is taken in any undefined plane; whereby they fail to attain the precision in three dimensions.

Generally followed protocols of knee replacement surgeries violates medullary canal and thereby generates the high risk of embolism.

Many of the jigs are complicated to use yet fail to effectively aid in knee replacement surgery to attain precision in implant placement.

Separate jigs are required for the steps of sizing and that of distal cut to be taken one after the other; making the knee replacement surgery time consuming; which in-turn requires the knee to be kept open for a longer time substantially increasing the chances of infection.

The available sets of jigs fail to minimize the bone loss.

There are multiple instrumentation for doing of multiple tasks of sizing and distal cuts, thereby increasing number of instruments to be prepared and sterilized. Thus there is increased spending of resources in terms of energy inputs and labor.

They lack in accuracy.

They are not reliable.

They fail to facilitate the doctor to work with acumen.

They fail to aid the knee replacement surgery that can in turn provide Patient satisfaction.

OBJECTIVES OF THE INVENTION

The main objective of the present invention is to provide jig for guiding placement of femoral component of the implant in a knee replacement surgery that enables to attain precision in placement of femoral component of the implant on the femur in terms of position and alignment; wherein said precision is attained in three dimensions in contrast to the generally followed protocols of knee replacement surgeries that work on two dimensions.

Another objective of the present invention is to provide jig for guiding placement of femoral component of the implant in a knee replacement surgery avoids intrusion of the intramedullary canal substantially decreasing the risks of embolism.

Yet another objective of the present invention is to provide jig for guiding placement of femoral component of the implant in a knee replacement surgery that is simple to use yet effectively aids knee replacement surgery to attain precision in implant placement.

Yet another objective of the present invention is to provide jig for guiding placement of femoral component of the implant in a knee replacement surgery whereby both the steps of sizing and that of distal cut are taken care at same time; making the knee replacement surgery less time consuming; which in-turn requires the knee to be kept open for a lesser time substantially decreasing the chances of infection.

Another objective of the present invention is to provide jig for guiding placement of femoral component of the implant in a knee replacement surgery with precision in three dimensions to help minimize the bone loss.

Yet another objective of the present invention is to provide jig for guiding placement of femoral component of the implant in a knee replacement surgery which enables doing of multiple tasks of sizing and distal cuts together, thereby reducing number of instruments to be prepared and sterilized, saving resources in terms of energy inputs and labor.

Yet another objective of the present invention is to provide a jig for guiding placement of femoral component of the implant in a knee replacement surgery which is highly accurate.

Yet another objective of the present invention is to provide a jig for guiding placement of femoral component of the implant in a knee replacement surgery which is reliable.

Yet another objective of the present invention is to provide a jig for guiding placement of femoral component of the implant in a knee replacement surgery which facilitates the doctor to work with acumen.

Yet another objective of the present invention is to provide jig for guiding placement of femoral component of the implant in a knee replacement surgery which aids in knee replacement surgery to enhance Patient satisfaction.

BRIEF DESCRIPTION OF DRAWINGS

| FIG. 1-1 | Shows fragmented view of present jig for guiding placement of femoral component of the implant in a knee replacement surgery |
| FIG. 1.2 | Shows perspective front view of present jig for guiding placement of femoral component of the implant in a knee replacement surgery |
| FIG. 1.3 | Shows perspective back view of present jig for guiding placement of femoral component of the implant in a knee replacement surgery |
| FIG. 1.4 | Shows axial view of present jig for guiding placement of femoral component of the implant in a knee replacement surgery; highlighting contact five points and illustrating rotation control. |
| FIG. 1.5 | Shows coronal view of present jig for guiding placement of femoral component of the implant in a knee replacement surgery; illustrating varus-valgus control. |
| FIG. 1.6 and FIG. 1.7 | Shows sagittal view of present jig for guiding placement of femoral component of the implant in a knee replacement surgery; illustrating flexion-extension control. |
| FIG. 2.1 | Shows fragmented view of the first embodiment of present jig for guiding placement of femoral component of the implant in a knee replacement surgery |
| FIG. 2.2 | Shows perspective front view of the first embodiment of present jig for guiding placement of femoral component of the implant in a knee replacement surgery |
| FIG. 2.3 | Shows perspective back view of the first embodiment of present jig for guiding placement of femoral component of the implant in a knee replacement surgery |
| FIG. 2.4 | Shows axial view of the first embodiment of present jig for guiding placement of femoral component of the implant in a knee replacement surgery; highlighting contact five points and illustrating rotation control. |
| FIG. 2.5 | Shows coronal view of the first embodiment of present jig for guiding placement of femoral component of the implant in a knee replacement surgery; illustrating varus-valgus control. |
| FIG. 2.6 and FIG. 2.7 | Shows sagittal view of the first embodiment of present jig for guiding placement of femoral component of the implant in a knee replacement surgery; illustrating flexion-extension control. |
| FIG. 3.1 | Shows fragmented view of the second embodiment of present jig for guiding placement of femoral component of the implant in a knee replacement surgery |
| FIG. 3.2 | Shows perspective front view of the second embodiment of present jig for guiding placement of femoral component of the implant in a knee replacement surgery |
| FIG. 3.3 | Shows perspective back view of the second embodiment of present jig for guiding placement of femoral component of the implant in a knee replacement surgery |
| FIG. 3.4 | Shows axial view of the second embodiment of present jig for guiding placement of femoral component of the implant in a knee replacement surgery; highlighting five contact points and illustrating rotation control. |
| FIG. 3.5 | Shows coronal view of the second embodiment of present jig for guiding placement of femoral component of the implant in a knee replacement surgery; illustrating varus-valgus control. |
| FIG. 3.6 and FIG. 3.7 | Shows sagittal view of the second embodiment of present jig for guiding placement of femoral component of the implant in a knee replacement surgery; illustrating flexion-extension control. |
| FIG. 4.1, FIG. 4.2 and FIG. 4.3 | Illustrates the third embodiment of the present jig for guiding placement of femoral component of the implant in a knee replacement surgery. |

Wherein:

Meaning of Reference numerals of said component parts of present invention:

| J | Present jig for guiding placement of femoral component of the implant in a knee replacement surgery or present Jig. |
| PP | Posterior paddles |
| PPS | Posterior slots for bushings (in Posterior paddles) |
| PBU | Posterior Bushing |
| DB | Distal block |
| DBS | Distal slots for bushings (in Distal block) |
| DBM | Distal slots for marking |
| DBU | Distal bushing |
| DBB | Distal block for bushing |
| DMB | Distal Marking block |
| AP | Anterior probe with adjustable height |
| PB | Probe |
| MC | Measuring cylinder |
| SMC | slots for placing measuring cylinder |
| LB | Locking bolt |
| AB | Anterior cutting block (for cutting distal femur) |
| SL | Slot for saw blade |
| HO | Holes |
| h1 | First height |
| h2 | Second height |
| MLP | medio-lateral probes |

Additional References (not the Part of Present Jig)

| P1 | Distal lateral condyle |
| P2 | Distal medial condyle |
| P3 | Posterior lateral condyle |
| P4 | Posterior medial condyle and |
| P5 | Distal anterior cortex |

SUMMARY OF THE INVENTION

Referring to FIGS. 1.1 to 1.7, 2.1 to 2.7 and 3.1 to 3.7; the present jig for guiding placement of femoral component of the implant in a knee replacement surgery (J) mainly comprises of:

Posterior paddles (PP)
Posterior slots for bushings (in Posterior paddles) (PPS)
Posterior Bushing (PBU)
Distal block (DB)
Distal slots for bushings (in Distal block) (DBS)
Distal bushing (DBU)
Distal slot for marking (DBM),
Distal block for bushing (DBB),
Distal Marking block (DMB),
Supporting Block (SB),
Plurality of holes (DHO),
Pair of stems (PS),
Slots for measuring cylinder (SMC),
Anterior probe with adjustable height (AP),
Probe (PB),
Measuring cylinder (MC),
Locking bolt (LB), Anterior cutting block (for cutting distal femur) (AB),
Slot for saw blade (SL),
Holes (HO).

The present jig (J) uses measurements of displacement of Jig (J) of distal femur of the bone, in a knee replacement surgery; wherein, to achieve precise cut as per the values of depth of cuts obtained from a system for obtaining optimum fit implant as described in present applicant's another patent application, numbered as 3896/MUM2015.

This is to ensure precise position and alignment of the implant on the cut bone so as to achieve minimum bone loss and maximum patient satisfaction. While using the said obtained values, the present Jig (J) is used to obtain precise cuts on the distal femur in a knee replacement surgery. This requires precise placement of present Jig (J) on the distal femur in all three planes to enable precise cuts on the bone. This precise placement is ensured by the precisely measured (in millimeters) bushings used to create rotations in different plane. Said rotations are controlled by the present Jig (J) as under:

Rotation in axial plane: internal and external rotations are controlled by displacement of the posterior bushings (PBU) in 1 mm increment on the Posterior paddles (PP). (FIG. 1.4, 2.4, 3.4)

Similarly, rotations in coronal plane: varus or valgus are controlled by displacement of distal bushing (DBU) in 1 mm increment on the distal block (DB). (FIG. 1.5, 2.5, 3.5)

The rotations in the sagittal plane: flexion or extension are controlled by displacement in 1 mm increment on the anterior probe (AP). This is measured displacement of probe (PB) in the measuring cylinder (MC). (FIG. 1.6, 1.7, 2.6, 2.7, 3.6, 3.7)

Thus, the present Jig (J) uses measurements in millimeters (mm) in all three planes instead of the generally used angles in degrees (Refer prior art) in an undefined plane.

When the present Jig (J) is placed on the distal femur, it comes in contact with the bone at different points. The points are termed herein after as contact points. Said contact points are used as reference points to take precise measurements while adjusting the Jig to precise position so as to take precise cuts. Said contact points are preferably five or more than five to achieve the precise adjustments of measurement.

Present description embodies five such contact points while achieving precise position and alignment of the present Jig (J) on the distal femur:
P1: Distal lateral condyle,
P2: Distal medial condyle,
P3: Posterior lateral condyle,
P4: Posterior medial condyle and
P5: distal anterior cortex.

These five points defines the five degrees of freedom:
(1) Internal and external rotation (rotation in axial plane) is controlled by points of contact on posterior medial condyle and posterior lateral condyle (P3 and P4) as shown in the FIGS. 1.4, 2.4 and 3.4.

(2) Varus and valgus (rotation in coronal plane) is controlled by points of contact on distal medial condyle and distal lateral condyle (P1 and P2) as shown in the FIGS. 1.5, 2.5 and 3.5.

(3) Flexion and extension (Rotation in sagittal plane) is controlled by points of contact on posterior medial condyle, posterior lateral condyle and anterior cortex (P3, P4 and P5), (refer FIGS. 1.6, 1.7, 2.6, 2.7, 3.6 and 3.7)

(4) Distal translation (Depth of cut, translation in axial plane) is controlled by points of contact on distal medial condyle and distal lateral condyle (P2 and P1) and (5) Antero-posterior translation (translation in sagittal plane) is controlled by points of contact on posterior medial condyle, posterior lateral condyle and distal anterior cortex (P4, P3 and P5).

DESCRIPTION OF THE INVENTION

The present invention embodies a jig for guiding placement of femoral component of the implant in a knee replacement surgery (J). The present Jig (J) allows precise distal femoral cut with sizing and marking for subsequent femoral anterior, posterior and chamfer cuts simultaneously, saving surgery time. The present Jig (J) enables placement of the femoral component in all three planes with precision without violating the intramedullary canal. The present jig (J) is pre-assembled to ensure precision fit femoral implant for knee replacement based on difference of cuts in millimeters instead of the usual angle measurement in degrees.

The main embodiment of the present invention embodies a jig for guiding placement of femoral component of the implant in a knee replacement surgery (J) that mainly comprises of:
Posterior paddles (PP),
Posterior slots for bushings (PPS),
Posterior Bushing (PBU),
Distal block (DB),
Distal slots for bushings (DBS),
Distal bushing (DBU),
Anterior probe with adjustable height (AP),
Probe (PB),
Measuring cylinder (MC),
Locking bolt (LB),
Anterior cutting block (for cutting distal femur) (AB),
Slot for saw blade (SL),
Holes (HO).

Referring to FIGS. 1.1 to 1.7; shows the present jig for guiding placement of femoral component of the implant in a knee replacement surgery (J). Said Jig (J) has a pair of Posterior paddles (PP) made preferably of metal and having posterior slots (PPS) to accept posterior bushings (PBU). Said Jig (J) is placed on distal femur (for which knee replacement surgery is being done) such that said pair of Posterior paddles (PP) touches the posterior medial (P4) and posterior lateral (P3) femoral condyle as shown in FIG. 1.4, 2.4, 3.4, 1.6, 1.7, 2.6, 2.7, 3.6, 3.7. The points of contact (P4 and P3) on the posterior medial and posterior lateral femoral condyles represent the posterior condylar axis (see FIG. 1.4). The precise rotation (internal or external rotation) of the femoral component is determined by rotating the femoral component axis by rotating the present Jig (J) further posteriorly from the point of contact (posterior condylar axis) on either the lateral or medial posterior femur (P3 and P4) with the help of a bushing (PBU) of 1 mm increment. The amount of rotation (internal or external rotation) is measured by the offset required in form of the bushing (PBU) on the posterior medial or posterior lateral (P4 or P3) paddles in millimeters instead of degrees.

Further, a Distal block (DB) is provided with a pair of Distal slots for bushings (DBS) for accepting Distal bushing (DBU). Said Distal block (DB) is a continuous metal sheet at right angles to the Posterior paddles (PP). Said Distal block (DB) is to be placed over the distal medial (P2) and distal lateral femur (P1)(FIG. 1.5, 2.5, 3.5). The points of contact on the distal medial and distal lateral femoral condyles (P2 and P1) represent the distal femoral axis. The precise rotation (varus or valgus) of the femoral component is determined by rotating the femoral component axis by rotating the jig further medially or laterally from the point of contact on either the lateral or medial distal femoral condyle with the help of a bushing of 1 mm increment. The amount of rotation is measured by the offset required in form of the bushing on the distal block in millimeters instead of degrees.

Anterior probe with adjustable height (AP) having a sliding adjustable probe (PB) is provided wherein said probe (PB) is of variable height off the distal block (DB). It represents a fixed distance from the posterior paddles (PP) which are in continuation with the distal block (DB). It has a Measuring cylinder (MC) which is attached to said distal block (DB) through Locking bolt (LB). The distance between the tip of the anterior probe (PB) to the bushing on the posterior paddles (PP) represents the antero-posterior size of the femoral component (h1, h2) (refer FIG. 1.6, 1.7, 2.6, 2.7, 3.6, 3.7). The femoral component is placed in flexion by decreasing the antero-posterior distance. Similarly, the femoral component is placed in extension by increasing the antero-posterior distance. The size of the femoral component is also determined by the antero-posterior distance.

Thus, the present jig for guiding placement of femoral component of the implant in a knee replacement surgery (J) enables precise alignment and positioning of the femoral component in three dimensions by enabling precise adjustments of rotations in all three dimensions.

An anterior cutting block (for cutting distal femur) (AB) is also provided with Slot for saw blade (SL). This is a detachable block made preferably of metal attached to the distal block (DB). Once the rotations in all three dimensions are finalized and the jig (J) is placed with decided rotations, the distal femur cut is taken through the slot (SL) on this block (AB). Said anterior cutting block (AB) has holes (HO) to increase the depth of the distal femoral cut by 1, 2, or 3 mm.

OTHER EMBODIMENTS OF THE INVENTION

The present invention embodies other three major embodiments. These embodiments allow for simultaneous marking for the subsequent Jig for subsequent cuts of the femur, namely anterior posterior and chamfers. Thus, there is an additional provision in said embodiments to provide said markings through Distal Slots for marking (DBM). Said slots (DBM) are either placed on the same distal block (DB) along with slots for bushing (DBS) (as shown and described in first embodiment) or are placed as separate distal blocks (DBB and DMB as shown and described in second embodiment). Said embodiments are described herein below:

I. The First Embodiment

The jig for guiding placement of femoral component of the implant in a knee replacement surgery (J) of the first embodiment mainly comprises of:
Posterior paddles (PP),
Posterior slots for bushings (PPS),
Posterior Bushing (PBU),
Distal block (DB),
Distal slots for bushings (DBS),
Distal slot for marking (DBM),
Supporting block (SB),
plurality of holes (DHO),
pair of stems (PS),
Distal bushing (DBU),
Anterior probe with adjustable height (AP),
Probe (PB),
Measuring cylinder (MC),
Slots for measuring cylinder (SMC),
Locking bolt (LB),
Anterior cutting block (for cutting distal femur) (AB),
Slot for saw blade (SL),
Holes (HO).

The first embodiment (refer FIGS. 2.1 to 2.7) provides separable distal block (DB) which is separable from said posterior paddles (PP) with slots (PPS) for posterior bushings (PBU); wherein said Distal Block (DB) is attached to posterior paddles (PP) through plurality of holes (DHO) on lower portion of the distal block (DB) for accepting the pair of stems (PS) protruding out of the supporting block (SB) connected to the posterior paddles (PP). Said plurality of holes (DHO) are so arranged as to enable fixing of the distal block (DB) at different heights from the posterior paddles (PP). Said different heights are preferably 0, 1 mm, 2 mm, and 3 mm. Said height is determined by half the distance of the height of the bushing (PBU) placed on the posterior paddle (PP). This provision enables the marking for subsequent Jig at a pre-determined height from the posterior paddles (PP).

Further, said first embodiment involves the Distal slots for bushings (DBS) and Distal slots for marking (DBM) in same and continuous Distal block (DB). Distal bushings (DBU) are used in controlling the rotations are described herein above, by placing them in said slots for bushings (DBS). Further, marking Bushings available from the implant company are used to mark for the subsequent Jig through said Distal slots for marking (DBM).

Anterior probe with adjustable height (AP) having a sliding adjustable probe (PB) is provided wherein said probe (PB) is of variable height off the distal block (DB). It represents a fixed distance from the posterior paddles (PP) which are in continuation with the distal block (DB). It has a Measuring cylinder (MC) which is attached to said distal block (DB) through Locking bolt (LB). The distance between the tip of the anterior probe (PB) to the bushing on the posterior paddles (PP) represents the antero-posterior size of the femoral component (h1, h2) (refer FIG. 2.6, 2.7). The femoral component is placed in flexion by decreasing the antero-posterior distance. Similarly, the femoral component is placed in extension by increasing the antero-posterior distance. The size of the femoral component is also determined by the antero-posterior distance.

Additionally, said embodiment provides plurality of slots for placing measuring cylinder (SMC) wherein said slots (SMC) are used to place the measuring cylinder (MC) at different heights so as to decrease the working length of the anterior probe (PB). Anterior cutting block (AB) is attached at a fixed height on the distal block (DB).

An anterior cutting block (for cutting distal femur) (AB) is also provided with Slot for saw blade (SL). This is a detachable block made preferably of metal attached to the distal block (DB). Once the rotations in all three dimensions are finalized and the jig (J) is placed with decided rotations, the distal femur cut is taken through the slot (SL) on this block (AB). Said anterior cutting block (AB) has holes (HO) to increase the depth of the distal femoral cut by 1, 2, or 3 mm.

II. The Second Embodiment

The second embodiment (refer FIGS. 3.1 to 3.7) provides a jig for guiding placement of femoral component of the implant in a knee replacement surgery (J) which comprises of:

Posterior paddles (PP),
Posterior slots for bushings (PPS),
Posterior Bushing (PBU),
Distal block for bushing (DBB),
Distal slots for bushings (DBS),
Distal Marking block (DMB),
Distal slot for marking (DBM),
Distal bushing (DBU),
Anterior probe with adjustable height (AP),
Probe (PB),
Measuring cylinder (MC),
Locking bolt (LB),
Anterior cutting block (for cutting distal femur) (AB),
Slot for saw blade (SL),
Holes (HO).

Said Jig (J) has said pair of posterior paddles (PP) connected at right angles to the Distal Block for Bushing (DBB). Said Block (DBB) has distal slots for bushing (DBS) for accepting the distal bushings (DBS). The distal slots for marking (DBM) are provided on a separate block namely distal marking block (DMB). Anterior probe with adjustable height (AP) has said measuring cylinder (MC), which is attached to said Distal Block for Bushing (DBB). The distal marking block (DMB) slides on the measuring cylinder (MC). Said marking block (DBM) is fixed at a pre-determined height on said measuring cylinder (MC) through a locking bolt (LB). The anterior probe (PB) is also fixed to the distal marking block (DMB). Thus, the measurement on the measuring cylinder (MC) reflects the height (h1, h2) (refer FIG. 3.6, 3.7) from the tip of the probe (PB) to the bushing (PBU) on the posterior paddles (PP). The Anterior cutting block (AB) is attached at a fixed height on the distal marking block (DMB).

III. The Third Embodiment

The third embodiment provides a pair of medio-lateral probes (MLP) to be placed on distal block (DB) or the Distal block for bushing (DBB) or distal marking block (DMB) of the embodiments described herein above. The probes (MLP) define the sixth degree of freedom. They control medio-lateral placement of the implant (translation in the coronal plane). Thus, all six degrees of freedom are controlled by said embodiment. (FIG. 4)

Having described what is considered the best form presently contemplated for embodying the present invention, various alterations, modifications, and/or alternative applications of the invention for any system will be promptly apparent to those skilled in the art. Therefore, it is to be understood that the present invention is not limited to the practical aspects of the actual preferred embodiments hereby described and that any such modifications and variations must be considered as being within the spirit and the scope of the invention, as described in the above description.

WORKING OF THE INVENTION

The analysis for optimum fit implant and its optimum position is derived from the system for obtaining optimum fit implant as described in patent application number 3896/MUM2015 or a similar system. The depth of cuts on the distal femur and posterior femur along with the antero-posterior distance is obtained from the said system. These are used to calculate the placement and the size of the bushings.

For the distal bushings: The difference in the depth of cuts on distal medial and distal lateral femur gives the size of the bushing (DBU) to be used on the distal femur. The bushing is placed on the smaller cut side in terms of medial or lateral placement on the distal femur.

For the posterior bushings: Similarly, the difference in the depth of cuts on posterior medial and posterior lateral femur gives the size of the bushing (PBU) to be used on the posterior femur. The bushing (PBU) is placed on the smaller cut side in terms of medial or lateral placement on the posterior femur.

The antero-posterior distance gives the height of the anterior probe to be adjusted in the measuring cylinder (MC).

From the said data, the bushings of the desired size are placed first on the medial or lateral distal block and posterior paddles (PP). The height of the anterior probe (PB) is adjusted according to the antero-posterior distance derived from the said system. The probe is attached to the distal block (DB). The assembled jig (J) is placed on the femur ensuring contact at the following five points: (1) posterior paddle with or without the bushing on posterior-medial condyle, (2) posterior paddle with or without the bushing on the posterior lateral condyle, (3) distal block with or without the bushing on distal medial condyle, (4) distal block with or without the bushing on distal lateral condyle and (5) tip of anterior probe on the anterior cortex. The anterior distal cutting block is then, fixed to the femur with pins. The remaining jig is then removed. The distal femoral cut is checked clinically to assess the cuts. It has the additional option of +/−2, +/−4 mm or +/−6 mm cut for increasing or decreasing the depth of the distal femur resection.

In first embodiment of the jig, besides the above steps, another bushing of the desired size of the implant as provided by the implant company is placed in the slots in the distal block with slots for marking subsequent femur cuts. The placement of the subsequent jig is marked with a drill or a pin. The distal anterior cutting block is left in place and the remaining jig is detached and removed. The distal femoral cut is made after clinically assessing the depth. It has the additional option of +/−2, +/−4 mm or +/−6 mm cut for increasing or decreasing the depth of the distal femur resection.

In the second embodiment of the jig, besides the first steps detailed above, the placement of the subsequent jig is marked directly through the holes provided in the block with slots for marking subsequent femur cuts.

The slot on the anterior distal cutting block is then, used to take the distal femur cut.

Example 1

For patient A, LQS from implant company ZIN was the optimum implant derived by using the system for obtaining optimum fit implant as described in patent application number 3896/MUM2015 or a similar system. The values derived were implant size D, the distal femoral cuts were 9 mm on the medial side and 7 mm on the lateral side. The posterior cuts were 8 mm on the medial side and 6 mm on the lateral side. As company ZIN was selected, the jig (J) of the first embodiment was used. Thus, a 2 mm bushing was used on the lateral side distally (9−7=2 and smaller side was lateral) and another 2 mm bushing was used on the lateral side posteriorly (8−6=2 and smaller side was lateral). The anterior height given was 48 mm. the probe (PB) was fixed at 48 mm. The assembly was placed at distal femur ensuring the five point contact. The distal anterior cutting block was fixed with 2 pins. The remaining jig was removed and the distal cut was taken through the slot in the distal anterior cutting block.

| COMPANY | | GENERIC | | | Distal cut only | | | | | |
|---|---|---|---|---|---|---|---|---|---|---|
| Pat No. | Lat Dist | Med Dist | Bush Dist | Bush side | Lat Post | Med Post | Bush Dist | Bush side | Ant Dist | Probe |
| 1 | 8 | 7 | 1 | Med | 7 | 9 | 2 | Med | 48 | 48 |
| 2 | 10 | 8 | 2 | Med | 8 | 10 | 2 | Med | 53 | 53 |
| 3 | 9 | 6 | 3 | Med | 8 | 10 | 2 | Med | 59 | 59 |
| 4 | 9 | 10 | 1 | Lat | 7 | 9 | 2 | Med | 46 | 46 |
| 5 | 8 | 10 | 2 | Lat | 6 | 8 | 2 | Med | 49 | 49 |
| 6 | 9 | 9 | 0 | 0 | 8 | 10 | 2 | Med | 55 | 55 |
| 7 | 8 | 9 | 1 | Lat | 6 | 10 | 3 | Med | 54 | 54 |
| 8 | 6 | 8 | 2 | Lat | 7 | 9 | 2 | Med | 51 | 51 |
| 9 | 9 | 11 | 2 | Lat | 6 | 10 | 4 | Med | 52 | 52 |
| 10 | 8 | 8 | 0 | 0 | 9 | 11 | 2 | Med | 64 | 64 |

Example 2

For patient A, NRX from implant company STY was the optimum implant derived by using the system for obtaining optimum fit implant as described in patent application number 3896/MUM2015 or a similar system. The values derived were implant size 7, the distal femoral cuts were 9 mm on the medial side and 7 mm on the lateral side. The posterior cuts were 8 mm on the medial side and 6 mm on the lateral side. As company STY was selected, the jig (J) of the first embodiment was used. Thus, a 2 mm bushing was used on the lateral side distally (9−7=2 and smaller side was lateral) and another 2 mm bushing was used on the lateral side posteriorly (8−6=2 and smaller side was lateral). The anterior height given was 53 mm. The posterior paddles (PP) were attached at 1 mm as the posterior bushing was 2 mm. The probe (PB) was attached in the slots for placing measuring cylinder (SMC) of 45 mm and placed at 7 mm because 1 mm was already covered by shifting the distal block by 1 mm. The assembly was placed at distal femur ensuring the five point contact. The size 7 bushing from company STY was placed in the distal slot for marking (DBM). The distal anterior cutting block was fixed with 2 pins. The subsequent Jig placement was marked by drilling through the company bushing placed in the distal block for marking (DBM). The remaining jig was removed and the distal cut was taken through the slot in the distal anterior cutting block. This was then removed and the size 7 cutting block from STY was placed to complete the femoral cuts.

Similar examples are shown in the table attached below:

Example 3

For patient B, DES from implant company MER was the optimum implant derived by using the system for obtaining optimum fit implant as described in patent application number 3896/MUM2015 or a similar system. The values derived were implant size D, the distal femoral cuts were 8 mm on the medial side and 10 mm on the lateral side. The posterior cuts were 9 mm on the medial side and 6 mm on the lateral side. As company MER was selected, the jig (J) of the second embodiment was used. Thus, a 2 mm bushing was used on the medial side distally (10−8=2 and smaller side was medial) and another 3 mm bushing was used on the lateral side posteriorly (9−6=3 and smaller side was lateral). The anterior height given was 55 mm. The probe (PB) was locked at 55 mm with the help of the locking bolt. The assembly was placed at distal femur ensuring the five point contact. The distal anterior cutting block was fixed with 2 pins. The subsequent Jig placement was marked by drilling through the company bushing placed in the distal block for marking (DBM). The remaining jig was removed and the distal cut was taken through the slot in the distal anterior cutting block. This was then removed and the size D cutting block from MER was placed to complete the femoral cuts.

| COMPANY | | | | | | | | | | | | | |
|---|---|---|---|---|---|---|---|---|---|---|---|---|---|
| Pat No. | Lat Dist | Med Dist | Bush Dist | Bush Side | Lat Post | Med Post | Bush Dist | Bush side | Ant Dist | Post Padd | Slot | Probe | Comp Bush |
| 1 | 8 | 7 | 1 | Med | 7 | 9 | 2 | Med | 48 | 1 | 45 | 2 | 5 |
| 2 | 10 | 8 | 2 | Med | 8 | 10 | 2 | Med | 53 | 1 | 45 | 7 | 7 |
| 3 | 9 | 6 | 3 | Med | 8 | 10 | 2 | Med | 59 | 1 | 55 | 3 | 9 |
| 4 | 9 | 10 | 1 | Lat | 7 | 9 | 2 | Med | 46 | 1 | 45 | 0 | 4 |
| 5 | 8 | 10 | 2 | Lat | 6 | 8 | 2 | Med | 49 | 1 | 45 | 3 | 6 |
| 6 | 9 | 9 | 0 | 0 | 8 | 10 | 2 | Med | 55 | 1 | 45 | 9 | 8 |
| 7 | 8 | 9 | 1 | Lat | 6 | 10 | 3 | Med | 54 | 1 | 45 | 8 | 8 |
| 8 | 6 | 8 | 2 | Lat | 7 | 9 | 2 | Med | 51 | 1 | 45 | 5 | 7 |
| 9 | 9 | 11 | 2 | Lat | 6 | 10 | 4 | Med | 52 | 2 | 45 | 6 | 7 |
| 10 | 8 | 8 | 0 | 0 | 9 | 11 | 2 | Med | 64 | 1 | 55 | 8 | 11 |

Similar examples are shown in the table attached below.

| COMPANY | | | | | | MER | | | | |
|---|---|---|---|---|---|---|---|---|---|---|
| Pat No. | Lat Dist | Med Dist | Bush Dist | Bush side | Lat Post | Med Post | Bush Dist | Bush side | Ant Dist | Probe |
| 1 | 8 | 7 | 1 | Med | 7 | 9 | 2 | Med | 48 | 48 |
| 2 | 10 | 8 | 2 | Med | 8 | 10 | 2 | Med | 53 | 53 |
| 3 | 9 | 6 | 3 | Med | 8 | 10 | 2 | Med | 59 | 59 |
| 4 | 9 | 10 | 1 | Lat | 7 | 9 | 2 | Med | 46 | 46 |
| 5 | 8 | 10 | 2 | Lat | 6 | 8 | 2 | Med | 49 | 49 |
| 6 | 9 | 9 | 0 | 0 | 8 | 10 | 2 | Med | 55 | 55 |
| 7 | 8 | 9 | 1 | Lat | 6 | 10 | 3 | Med | 54 | 54 |
| 8 | 6 | 8 | 2 | Lat | 7 | 9 | 2 | Med | 51 | 51 |
| 9 | 9 | 11 | 2 | Lat | 6 | 10 | 4 | Med | 52 | 52 |
| 10 | 8 | 8 | 0 | 0 | 9 | 11 | 2 | Med | 64 | 64 |

FIG. 1.5 shows angle A1. FIG. 2.4 shows angle A2. FIG. 2.5 shows angle A3. FIG. 3.4 shows angle A4. FIG. 3.5 shows angle A5.

The invention claimed is:

1. A jig for guiding placement of femoral component of the implant in a knee replacement surgery (J) mainly comprises of:
Posterior paddles (PP),
Posterior slots for bushings (in Posterior paddles) (PPS),
Posterior Bushing (PBU),
Distal block (DB),
Distal slots for bushings (in Distal block) (DBS),
Distal bushing (DBU),
Anterior probe with adjustable height (AP),
Probe (PB),
Measuring cylinder (MC),
Locking bolt (LB),
Anterior cutting block (for cutting distal femur) (AB),
Slot for saw blade (SL),
Holes (HO);
Said Jig (J) has a pair of Posterior paddles (PP) made preferably of metal and having posterior slots (PPS) to accept posterior bushings (PBU); said pair of Posterior paddles (PP) touches the posterior medial (P4) and posterior lateral (P3) femoral condyle while placing present jig (J) on distal femur wherein present jig (J) rotated posteriorly from the point of contact (posterior condylar axis) on either the lateral or medial posterior femur (P3 and P4) with the help of a bushing (PBU) of 1 mm increment to achieve precise rotation;
said Distal block (DB) is provided with a pair of Distal slots for bushings (DBS) for accepting Distal bushing (DBU) wherein said Distal block (DB) is a continuous metal sheet at right angles to the Posterior paddles (PP); said Distal block (DB) touches distal medial (P2) and distal lateral femur (P1) while it be Jig (J) is placed on the distal femur wherein the present jig (J) is rotated medially or laterally from the point of contact on either the lateral or medial distal femoral condyle with the help of a bushing (DBU) of 1 mm increment to achieve precision;
said anterior probe with adjustable height (AP) having a sliding adjustable probe (PB) is provided wherein said probe (PB) is of variable height off the distal block (DB); it has a Measuring cylinder (MC) which is attached to said distal block (DB) through Locking bolt (LB); wherein the femoral component is placed in flexion by decreasing the antero-posterior distance; similarly, the femoral component is placed in extension by increasing the antero-posterior distance;
an anterior cutting block (for cutting distal femur) (AB) is also provided with Slot for saw blade (SL) for taking femur cuts; this is a detachable block (AB) made preferably of metal attached to the distal block (DB); said anterior cutting block (AB) has holes (HO) to increase the depth of the distal femoral cut by 1, 2, or 3 mm.

2. The present jig for guiding placement of femoral component of the implant in a knee replacement surgery (J) as claimed in claim 1, wherein the amount of rotation (internal or external rotation) is measured by the offset required in form of the bushing (PBU) on the posterior medial or posterior lateral (P4 or P3) paddles in millimeters instead of degrees.

3. A jig for guiding placement of femoral component of the implant in a knee replacement surgery (J) comprising of:
Posterior paddles (PP),
Posterior slots for bushings (PPS),
Posterior Bushing (PBU),
Distal block for bushing (DBB),
Distal slots for bushings (DBS),
Distal Marking block (DMB),
Distal slot for marking (DBM),
Distal bushing (DBU),
Anterior probe with adjustable height (AP),
Probe (PB),
Measuring cylinder (MC),
Locking bolt (LB),
Anterior cutting block (for cutting distal femur) (AB),
Slot for saw blade (SL),
Holes (HO);
Said Jig (J) has said pair of posterior paddles (PP) connected at right angles to the Distal Block for Bushing (DBB) and said Block (DBB) has distal slots for bushing (DBS) and the distal slots for marking (DBM) are provided on a separate block namely distal marking block (DMB);
the measuring cylinder (MC) is attached to said Distal Block for Bushing (DBB) and the distal marking block (DMB) slides on the measuring cylinder (MC) wherein Said marking block (DBM) is fixed at a pre-determined height on said measuring cylinder (MC) through a locking bolt (LB); further, the anterior probe (PB) is also fixed to the distal marking block (DMB);
the Anterior cutting block (AB) is attached at a fixed height on the distal marking block (DMB).

4. A jig for guiding placement of femoral component of the implant in a knee replacement surgery (J) as claimed in claim 3; having a pair of medio-lateral probes (MLP) to be placed on distal block (DB) or the Distal block for bushing (DBB) or distal marking block (DMB).

5. The present jig for guiding placement of femoral component of the implant in a knee replacement surgery (J) as claimed in claim 3, wherein the amount of rotation (internal or external rotation) is measured by the offset required in form of the bushing (PBU) on the posterior medial or posterior lateral (P4 or P3) paddles in millimeters instead of degrees.

\* \* \* \* \*